US012024580B2

(12) United States Patent
Grießer et al.

(10) Patent No.: US 12,024,580 B2
(45) Date of Patent: Jul. 2, 2024

(54) RESIN COMPOSITION SUITABLE FOR PRINTING AND PRINTING METHODS

(71) Applicant: MONTANUNIVERSITÄT LEOBEN, Leoben (AT)

(72) Inventors: Thomas Grießer, St. Peter-Freienstein (AT); Matthias Edler, Gratwein-Straßengel (AT); Delara Gabriela Hartmann, Nümbrecht (DE); Andreas Bernhard Oesterreicher, Edlibach (CH)

(73) Assignee: MONTANUNIVERSITÄT LEOBEN, Leoben (AT)

( * ) Notice: Subject to any disclaimer, the term of this patent is extended or adjusted under 35 U.S.C. 154(b) by 104 days.

(21) Appl. No.: 17/260,960

(22) PCT Filed: Jul. 18, 2019

(86) PCT No.: PCT/EP2019/069338
§ 371 (c)(1),
(2) Date: Jan. 15, 2021

(87) PCT Pub. No.: WO2020/016343
PCT Pub. Date: Jan. 23, 2020

(65) Prior Publication Data
US 2021/0317241 A1   Oct. 14, 2021

(30) Foreign Application Priority Data
Jul. 20, 2018  (GB) ..................................... 1811896

(51) Int. Cl.

| C08F 38/00 | (2006.01) |
|---|---|
| B29C 64/129 | (2017.01) |
| B29C 64/188 | (2017.01) |
| B29C 64/35 | (2017.01) |
| B33Y 70/00 | (2020.01) |
| B33Y 80/00 | (2015.01) |
| B41M 5/00 | (2006.01) |
| C08F 2/44 | (2006.01) |
| C08F 2/50 | (2006.01) |
| C08F 228/00 | (2006.01) |
| C08K 5/5317 | (2006.01) |
| C09D 11/101 | (2014.01) |
| C09D 11/38 | (2014.01) |
| B33Y 10/00 | (2015.01) |

(52) U.S. Cl.
CPC ............ *C08F 38/00* (2013.01); *B29C 64/129* (2017.08); *B29C 64/188* (2017.08); *B29C 64/35* (2017.08); *B33Y 70/00* (2014.12); *B33Y 80/00* (2014.12); *B41M 5/0023* (2013.01); *C08F 2/44* (2013.01); *C08F 2/50* (2013.01); *C08F 228/00* (2013.01); *C08K 5/5317* (2013.01); *C09D 11/101* (2013.01); *C09D 11/38* (2013.01); *B33Y 10/00* (2014.12)

(58) Field of Classification Search
CPC .......... A61L 27/14; A61L 27/26; A61L 27/18; A61L 27/54; A61L 2300/404; B29C 64/00; B29C 64/129; B29C 64/188; B29C 64/35; B33Y 10/00; B33Y 70/00; B33Y 80/00; B41M 5/0023; C08F 4/44; C08F 4/50; C08F 38/00; C08F 220/04; C08F 228/00; C08F 238/00; C08G 75/045; C08G 75/26; C08K 3/32; C08K 5/5317; C08L 69/00; C08L 71/00; C08L 101/16; C09D 5/14; C08D 11/101; C08D 11/38
See application file for complete search history.

(56) References Cited

U.S. PATENT DOCUMENTS

| 3,725,228 | A |  | 4/1973 | Kehr et al. |
| 5,100,929 | A |  | 3/1992 | Jochum et al. |
| 6,045,607 | A |  | 4/2000 | Breton et al. |
| 8,848,856 | B2 |  | 9/2014 | Eckardt et al. |
| 10,202,485 | B2 | * | 2/2019 | Murakami ....... B29D 11/00038 |
| 11,591,438 | B2 | * | 2/2023 | Hoffmann ............. C08F 283/12 |
| 2013/0084543 | A1 | * | 4/2013 | Liska ..................... C08L 33/06 604/20 |
| 2015/0252234 | A1 |  | 9/2015 | Okazaki et al. |
| 2016/0280954 | A1 |  | 9/2016 | Walther et al. |

(Continued)

FOREIGN PATENT DOCUMENTS

| EP | 2980113 A1 | 2/2016 |
| EP | 3066161 B1 | 7/2017 |

(Continued)

OTHER PUBLICATIONS

Wendel et al.: "Additive Processing of Polymers"; Macromol. Mater. Eng., 2008, 293, pp. 799-809.
Ligon-Auer et al.: "Toughening of photo-curable polymer networks: a review"; Polymer Chemistry, 2016, 7, pp. 257-286.
Husár et al.: "Biomaterials Based on Low Cytotoxic Vinyl Esters for Bone Replacement Application"; Journal of polymer science part A: Polymer Chemistry, 2011, 49, pp. 4927-4934.
Ye S. et al.: "Reaction Kinetics and Reduced Shrinkage Stress of Thiol-Yne-Methacrylate and Thiol-Yne-Acrylate Ternary Systems"; Macromolecules, 2011, 44, pp. 9084-9090.

(Continued)

*Primary Examiner* — Sanza L. McClendon
(74) *Attorney, Agent, or Firm* — Lewis Roca Rothgerber Christie LLP

(57) ABSTRACT

Embodiments of the invention relate to a resin composition, in particular suitable for printing, a kit comprising components of the resin composition, printing methods, a polymer obtained by the printing methods, an article comprising or formed from the polymer, uses thereof, and a composition. The resin composition comprises at least one compound C1 having at least one terminal alkyne functional group; at least one compound C2 having at least two thiol functional groups; at least one compound C3 having at least one carbon-carbon double bond; at least one photoinitiator; and at least one stabilizer.

18 Claims, No Drawings

(56) References Cited

U.S. PATENT DOCUMENTS

| | | | | |
|---|---|---|---|---|
| 2016/0376453 A1* | 12/2016 | Hearon | ............... | C09D 11/30 |
| | | | | 428/339 |
| 2017/0291357 A1 | 10/2017 | Fong et al. | | |
| 2018/0171080 A1 | 6/2018 | Namiki et al. | | |
| 2019/0040175 A1 | 2/2019 | Onishi et al. | | |

FOREIGN PATENT DOCUMENTS

| | | | | | |
|---|---|---|---|---|---|
| GB | 2537770 | A | | 10/2016 | |
| JP | H02178205 | A | | 7/1990 | |
| JP | H1060114 | A | | 3/1998 | |
| JP | 5027836 | B2 | | 6/2012 | |
| JP | 2015086162 | A | | 5/2015 | |
| RU | 2346010 | C2 | | 2/2009 | |
| WO | 2005/049744 | A1 | | 6/2005 | |
| WO | 2008/074548 | A1 | | 6/2008 | |
| WO | 2009/132070 | A2 | | 10/2009 | |
| WO | 2010/141274 | A1 | | 12/2010 | |
| WO | 2012/103445 | A2 | | 8/2012 | |
| WO | 2012/126695 | A1 | | 9/2012 | |
| WO | WO-2012126695 | A1 | * | 9/2012 | ........... G03F 7/0037 |
| WO | 2013/052328 | A1 | | 4/2013 | |
| WO | WO-2013052328 | A1 | * | 4/2013 | ............. A61L 27/16 |
| WO | 2013/087427 | A1 | | 6/2013 | |
| WO | 2014061687 | A1 | | 4/2014 | |
| WO | 2014/070973 | A1 | | 5/2014 | |
| WO | WO-2014157664 | A1 | * | 10/2014 | ....... B29D 11/00038 |
| WO | 2015/084753 | A1 | | 6/2015 | |
| WO | 2015/158718 | A1 | | 10/2015 | |
| WO | WO-2015158718 | A1 | * | 10/2015 | ............. A61K 6/087 |
| WO | 2016194618 | A1 | | 12/2016 | |
| WO | 2017/063983 | A1 | | 4/2017 | |
| WO | 2017/064145 | A1 | | 4/2017 | |
| WO | 2017154428 | A1 | | 9/2017 | |
| WO | 2017223084 | A1 | | 12/2017 | |
| WO | 2018049302 | A1 | | 3/2018 | |

OTHER PUBLICATIONS

Lee T. Y. et al.: "Thiol-Allyl Ether-Methacrylate Ternary Systems. Evolution Mechanism of Polymerization-Induced Shrinkage Stress and Mechanical Properties"; Macromolecules, 2007, 40, pp. 1473-1479.
Lee T. Y. et al.: "Thiol-Allyl Ether-Methacrylate Ternary Systems. Polymerization Mechanism"; Macromolecules, 2007, 40, pp. 1466-1472.
Cramer N. B. et al.: "Investigation of thiol-ene and thiol-ene-methacrylate based resins as dental restorative materials"; Dental materials 26, 2010, pp. 21-28.
Cramer N. B. et al.: "Properties of methacrylate-thiol-ene formulations as dental restorative materials"; Dental Materials, 26, 2010, pp. 799-806.
A. J. Isquith et al.: "Surface-Bonded Antimicrobial Activity of an Organosilicon Quaternary Ammonium Chloride"; Applied and Environmental IMicrobiology, 1972, vol. 24, No. 6, pp. 859-863.
International Search Report and Written Opinion issued in corresponding International Application No. PCT/EP2019/069338, mailed Jan. 23, 2020, 17 pages.
International Preliminary Report on Patentability issued in corresponding International Application No. PCT/EP2019/069338, mailed Feb. 4, 2021.
Search Report Under Section 17(5) issued in corresponding German Application No. GB1811896.8, mailed Feb. 13, 2019, 4 pages.
European Office action for Application No. 19742350.2, dated Jan. 10, 2023, 3 pages.
Japanese Office action for Application No. 2021-525371, dated Mar. 24, 2023, 6 pages.
Russian Office action for Application No. 2021103009/04, dated Mar. 23, 2023, 20 pages.
Japanese Office action for Application No. 2021-525371, dated Aug. 15, 2023, 5 pages.
Canadian Examination Report for Application No. 3,107,051, dated Jan. 12, 2024, 7 pages.

* cited by examiner

RESIN COMPOSITION SUITABLE FOR PRINTING AND PRINTING METHODS

CROSS-REFERENCE TO RELATED APPLICATIONS

This application is the U.S. national phase of International Application No. PCT/EP2019/069338 filed 18 Jul. 2019 which designated the U.S. and claims priority to British Patent Application No. 1811896.8 filed 20 Jul. 2018, the entire contents of each of which are hereby incorporated herein by reference.

FIELD OF THE INVENTION

Embodiments of the invention relate to a resin composition, in particular suitable for printing, a kit comprising components of the resin composition, printing methods, a polymer obtained by the printing methods, an article comprising or formed from the polymer, uses thereof, and a composition.

BACKGROUND

Printing methods may serve for a large variety of purposes. In addition to traditional two-dimensional printing methods that are still widely used, three-dimensional printing methods have gained increasing interest over the past years. Initially developed for preparing prototypes, for instance for design purposes, three-dimensional (3D) printing methods are now more and more utilized for producing highly sophisticated and complex geometric structures that are brought to market as such, for instance in the automobile industry, for producing ornaments and in end-user appliances (Wendel et al., Macromol. Mater. Eng. 293 (2008) 799-809).

Among the known 3D printing methods, stereolithography (SLA) represents a very promising approach, since it attains a very high resolution that can hardly be attained with other techniques. This technique based on photopolymerization of liquid resins has a great potential for the manufacture of tailored shaped articles for the producing industry (among others, automotive, aviation, medical field) requiring a high fitting accuracy as well as high surface quality. However, the hitherto used materials in stereolithography do often not fulfill the required thermo-mechanical properties and are often brittle compared with technically relevant plastic materials (Ligon-Auer et al., Polym. Chem. 7 (2016) 257). Thus, they may be applied in prototyping, but the application of the produced shaped articles as fully operable parts is limited. In addition, commercially available resin compositions are mainly based on (meth)acrylate monomers, which are not suitable for the production of medical devices to be contacted with tissue due to their cytotoxicity (HusAr et. al, J. Polym. Sci. A Polym. Chem. 49 (2011) 4927).

Thus, the choice of commercially available printing resins suitable for stereolithography is still limited so that there is a need for the development of new materials and compositions.

OBJECTS OF THE INVENTION

In light of the foregoing, embodiments of the invention invention aims at overcoming the above described problems and drawbacks of hitherto available printing resins, in particular the restrictions thereof in terms of thermo-mechanical properties and suitability for use in medical or biomedical appliances. Thus, there may be a need to provide a novel resin composition which may be suitable for printing, in particular by means of stereolithography, and which may provide tailored shaped articles meeting the requirements of the producing industry in terms of thermo-mechanical properties, such as ductility, low shrinkage, dimensional stability under heat, and/or biocompatibility for medical or biomedical applications. Moreover, there may be a need to provide a procedure for cleaning 3D printed structures by means of completely removing residuals of non-cured UV resin without risk of deterioration of the printed structures.

SUMMARY OF THE INVENTION

The inventors have made diligent studies for solving these objects and have found that a resin composition comprising three types of monomers, namely a compound having a terminal alkyne functional group, a compound having at least two thiol functional groups and a compound having a carbon-carbon double bond, i.e. a thiol-yne-alkene system, may be polymerized in a thiol-yne-alkene reaction during a printing process upon irradiation in the presence of a photoinitiator and under high monomeric conversion (>90%) such that the resulting polymer may form a three-dimensional network having high homogeneity which may exhibit unique thermo-mechanical characteristics, such as a high ductility, a very good dimensional stability under heat and even a shape memory behaviour, as well as excellent biocompatibility and biodegradability (as appropriate), further offering the possibility of applying antimicrobial (nano) coatings. In particular, the inventors have found that the advantageous characteristics resulting from a step-growth polymerization, as it is the case in a thiol-yne reaction, such as a low shrinkage stress (resulting in a less brittle polymer article), and the advantageous characteristics resulting from a chain-growth polymerization, as it is the case in a radical alkene polymerization, such as an adjustable time of gelation, in particular a sufficiently short time of gelation appropriate for 3D printing, may be achieved in combination in a thiol-yne-alkene system, as described herein. Noteworthy in this regard, a low shrinkage stress and a short time of gelation are typically conflicting properties. In a mere thiol-yne system, the gel point is achieved at a relatively late stage of the polymerization reaction due to the step-growth mechanism, which enables that the shrinkage stress may be substantially relieved (thus, the resulting polymer may exhibit a low shrinkage stress), but which also leads to very long printing times. On the other hand, in a mere radical alkene polymerization, for instance when polymerizing pure (meth)acrylates, the gel point is achieved very quickly due to the chain-growth polymerization mechanism, so that very fast printing times may be realized, but very high shrinkage stress is generated in the network thus formed, so that the polymers tend to become brittle. The inventors have found that in a thiol-yne-alkene system, as described herein, both mechanisms may be combined enabling an adjustable time of gelation as well as superior (compared with a thiol-ene reaction) and also adjustable mechanical properties (such as heat deflection temperature (HDT) and modulus, see Examples 2 and 9). In addition, to maintain an appropriate viscosity so as to increase the storage stability, a stabilizer (in particular a combination of specific stabilizers) may be added to the resin composition. The inventors have further found that unreacted residual monomers may be efficiently removed from a (printed) polymer obtained by thiol-ene reaction and/or thiol-yne reaction by means of applying a cleaning solution containing an alkaline compound, a surfactant and an appropriate solvent. Without wishing to be bound by any theory, the inventors assume that due to an alkaline catalyzed thiol-ene reaction and/or thiol-yne reaction, residual monomers may be precipitated and the thus formed precipitates may be removed by the cleaning solution. Upon filtration of the cleaning solution (or otherwise removal of precipitates from the cleaning solution, such as by means of centrifugation or decantation), it may be reused in a further cleaning step.

Accordingly, an exemplary embodiment of the invention relates to a resin composition comprising:
at least one compound C1 having at least one terminal alkyne functional group;
at least one compound C2 having at least two thiol functional groups;
at least one compound C3 having at least one carbon-carbon double bond;
at least one photoinitiator; and
at least one stabilizer.

The resin composition as described herein is in particular suitable for printing, more specifically for use in stereolithography.

Accordingly, a further exemplary embodiment of the invention relates to the use of the resin composition as described herein as or in an ink.

The components of the resin composition as described herein may be in particular provided in a spatially separated manner, for instance in a kit, in particular a kit-of-parts. When the compound C1 having at least one terminal alkyne functional group and the compound C3 having at least one carbon-carbon double bond on the one hand and the compound C2 having at least two thiol functional groups on the other hand are provided in separate compositions (for instance spatially separated manner in a kit-of-parts), which are combined not until immediately prior to printing, a stabilizer may be dispensable (but may be nevertheless contained, for instance in smaller amounts).

Thus, an exemplary embodiment of the invention relates to a kit comprising: at least one compound C1 having at least one terminal alkyne functional group;
at least one compound C2 having at least two thiol functional groups;
at least one compound C3 having at least one carbon-carbon double bond;
at least one photoinitiator; and
optionally at least one stabilizer.

Furthermore, an exemplary embodiment of the invention relates to the use of the kit as described herein for preparing a resin composition for use as or in an ink.

As previously noted, when the compound C1 having at least one terminal alkyne functional group and the compound C3 having at least one carbon-carbon double bond on the one hand and the compound C2 having at least two thiol functional groups on the other hand are provided in separate compositions (for instance spatially separated manner in a kit-of-parts), which are combined not until immediately prior to printing, a stabilizer may be dispensable (but may be nevertheless contained, for instance in smaller amounts).

Thus, a further exemplary embodiment of the invention relates to a printing method comprising the steps of
providing a first ink portion comprising at least one compound C1 having at least one terminal alkyne functional group and at least one compound C3 having at least one carbon-carbon double bond;
providing a second ink portion comprising at least one compound C2 having at least two thiol functional groups;
wherein at least one of the first and the second ink portions further comprises at least one photoinitiator;
forming a resin composition from the first and the second ink portions, immediately followed by irradiating at least a part of the resin composition with an energy-carrying activation beam so as to cause polymerization of the at least a part of the resin composition and so as to obtain a polymer.

Moreover, an exemplary embodiment of the invention further relates to a printing method comprising the steps of
providing a resin composition as described herein; and
irradiating at least a part of the resin composition with an energy-carrying activation beam so as to cause polymerization of the at least a part of the resin composition and so as to obtain a polymer.

In addition, an exemplary embodiment of the invention relates to a polymer obtainable by the printing methods as described herein.

Moreover, an exemplary embodiment of the invention relates to an article comprising or formed from the polymer as described herein.

The polymer and the article obtained as described herein can be used for various appliances.

Accordingly, a further exemplary embodiment of the invention relates to the use of the polymer or of the article as described herein in a medical or biomedical application.

In addition, an exemplary embodiment of the invention relates to a composition comprising:
at least one compound C1 having at least one terminal alkyne functional group and/or at least one compound C3 having at least one carbon-carbon double bond;
at least one compound C2 having at least two thiol functional groups; and
at least one stabilizer selected from the group consisting of a radical scavenger, a phosphorous containing compound and a complexing agent.

Furthermore, an exemplary embodiment of the invention relates to a printing method comprising the steps of
providing a resin composition comprising at least one compound C1 having at least one terminal alkyne functional group and/or at least one compound C3 having at least one carbon-carbon double bond and at least one compound C2 having at least two thiol functional groups;
irradiating at least a part of the resin composition with an energy-carrying activation beam so as to cause polymerization of the at least a part of the resin composition and so as to obtain a polymer; and
contacting the polymer with a cleaning composition (e.g. a cleaning solution) comprising an alkaline compound, a surfactant and a solvent.

Other objects and many of the attendant advantages of embodiments of the invention will be readily appreciated and become better understood by reference to the following detailed description of embodiments.

DETAILED DESCRIPTION OF THE INVENTION

Hereinafter, details of embodiments of the invention and other features and advantages thereof will be described. However, the invention is not limited to the following specific descriptions, but they are rather for illustrative purposes only.

It should be noted that features described in connection with one exemplary embodiment or exemplary aspect may be combined with any other exemplary embodiment or exemplary aspect, in particular features described with any exemplary embodiment of the resin composition may be combined with any exemplary embodiment of a kit, a printing method, a polymer, an article, a composition or with any exemplary embodiment of uses thereof and vice versa, unless specifically stated otherwise.

Where an indefinite or definite article is used when referring to a singular term, such as "a", "an" or "the", a plural of that term is also included and vice versa, unless specifically stated otherwise, whereas the word "one" or the number "1", as used herein, typically means "just one" or "exactly one".

The expression "comprising", as used herein, includes not only the meaning of "comprising", "including" or "containing", but also encompasses "consisting essentially of" and "consisting of".

Unless specifically stated otherwise, the expressions "at least partially", "at least a partial" or "at least a part of", as used herein, may mean at least 5% thereof, in particular at least 10% thereof, in particular at least 15% thereof, in particular at least 20% thereof, in particular at least 25% thereof, in particular at least 30% thereof, in particular at least 35% thereof, in particular at least 40% thereof, in particular at least 45% thereof, in particular at least 50% thereof, in particular at least 55% thereof, in particular at least 60% thereof, in particular at least 65% thereof, in particular at least 70% thereof, in particular at least 75% thereof, in particular at least 80% thereof, in particular at least 85% thereof, in particular at least 90% thereof, in particular at least 95% thereof, in particular at least 98% thereof, and may also mean 100% thereof.

In a first aspect, an exemplary embodiment of the invention relates to a resin composition comprising:
  at least one compound C1 having at least one terminal alkyne functional group;
  at least one compound C2 having at least two thiol functional groups;
  at least one compound C3 having at least one carbon-carbon double bond;
  at least one photoinitiator; and
  at least one stabilizer.

The term "composition", as used herein, may in particular mean that the components (ingredients) of the composition are in close proximity with each other and/or that the components are (intensely) mixed with each other, for instance by using a mixer, a stirrer and/or by shaking, to thereby form the composition. In particular, the components of the compositions may be uniformly distributed or dispersed throughout within the composition. The composition may be in particular solid, semi-solid (pasty) or liquid, in particular a liquid solution or a semi-solid or liquid suspension.

The resin composition may in particular be a photo-reactive resin composition. The term "photo-reactive", as used herein, may in particular mean that the resin composition, in particular some or all of its components, undergo a (chemical) reaction upon irradiation with an energy-carrying activation beam, in particular with electromagnetic radiation.

The resin composition may be in particular suitable for printing (in particular by means of stereolithography), for instance in a printing method according to embodiments of the invention. Accordingly, the resin composition may be in particular used as an ink (a printing ink), i.e. the resin composition itself may be directly used as an ink. Likewise, the resin composition may be in particular used in an ink (a printing ink), i.e. as a component or an ingredient of an ink together with appropriate one or more further components or ingredients, typically used in an ink.

The resin composition comprises at least three monomers: at least one compound C1 (also referred to as "yne component" or "yne monomer"), at least one compound C2 (also referred to as "thiol component" or "thiol monomer") and at least one compound C3 (also referred to as "alkene component" or "alkene monomer"). As it is evident, the resin composition may contain more than one compound C1 (such as mixtures of different compounds C1), more than one compound C2 (such as mixtures of different compounds C2) and/or more than one compound C3 (such as mixtures of different compounds C3), as well as further ingredients or components, which will be described below.

The compound C1 has at least one terminal alkyne functional group.

The term "terminal alkyne functional group", as used herein and as commonly understood by a person skilled in the art, represents a moiety having a carbon-carbon triple bond wherein one of the carbon atoms binds to a hydrogen atom.

In other words, a terminal alkyne functional group may be represented by the general formula "—C≡C—H". The terminal alkyne functional group may also be present in protected form, for instance as a silyl (such as trimethylsilyl (TMS)) protected alkyne group and/or as a complex of the carbon-carbon triple bond with for instance dicobalt octacarbonyl. Appropriate deprotection (removal of the protecting group) should then be carried out, as it is well known to a person skilled in the art, prior to the use of the resin composition, for instance in a printing method or in any other intended use thereof where the terminal alkyne functional group is intended to take part in a thiol-yne-alkene reaction.

Besides the at least one terminal alkyne functional group, the structure of the compound C1 is not particularly limited and may include branched or linear (carbon) moieties, which may include various functional groups, as well as oligomeric or polymeric chains. In particular, the at least one compound C1 may comprise at least one group or moiety selected from a linear or branched, saturated or unsaturated, substituted or unsubstituted alkyl group; a linear or branched, saturated or unsaturated, substituted or unsubstituted heteroalkyl group; a saturated or unsaturated, substituted or unsubstituted cycloalkyl group; a saturated or unsaturated, substituted or unsubstituted heterocycloalkyl group; a substituted or unsubstituted aryl group; a substituted or unsubstituted heteroaryl group; a linear or branched, substituted or unsubstituted aralkyl group; a linear or branched, substituted or unsubstituted alkaryl group; an oligomer or a polymer.

The meaning of the terms "linear", "branched", "saturated", "unsaturated" and "unsubstituted", as used herein, corresponds to the respective well-established meanings thereof, as known to a person skilled in the art. The term "substituted", as used herein, means that one or more, in particular 1, 2, 3, 4, 5, 6, 7, 8, 9 or 10, hydrogen atom(s) of the respective groups are substituted by a substituent. Examples of suitable substituents, include halogen atoms, such as —F, —Cl, —Br, —I; —OH, hydroxyalkyl groups (ether), —SH, thioalkyl groups (thioether), =O, carboxyl groups (—COOH) and salts, esters and amides thereof, —NH$_2$, secondary amine groups, tertiary amine groups, nitrile groups and nitro groups. If two or more substituents are present, they may be the same or different and they may be bound to each other to form a ring. The terms "heteroalkyl group", "heterocycloalkyl group" or "heteroaryl group", respectively, represents an alkyl group, a cycloalkyl group or an aryl group, respectively, wherein one or more, in particular 1, 2, 3, 4, 5, 6, 7, 8, 9 or 10, carbon atoms are replaced by a hetero atom, such as O, N or S, in particular O and/or N. If more than one hetero atom is contained in a group, these hetero atoms may be the same or different.

Suitable examples of the alkyl group include $C_1$ to $C_{20}$ alkyl groups, in particular $C_2$ to $C_{10}$ alkyl groups, in particular $C_3$ to $C_a$ alkyl groups, in particular $C_4$ to $C_6$ alkyl groups.

Suitable examples of the cycloalkyl group include $C_3$ to $C20$ cycloalkyl groups, in particular $C_4$ to $C_{15}$ cycloalkyl groups, in particular $C_5$ to $C_{10}$ cycloalkyl groups, in particular $C_6$ to $C_8$ cycloalkyl groups.

Suitable examples of the aryl group include $C_6$ to $C_{20}$ aryl groups, in particular $C_6$ to $C_{16}$ aryl groups, in particular $C_6$ to $C_{14}$ aryl groups, in particular $C_6$ to $C_{10}$ aryl groups. In particular, the aryl group may be a phenyl group.

An "aralkyl group", as used herein, denotes a group having an aliphatic and an aromatic moiety, wherein the aliphatic moiety binds to the terminal alkyne functional group or any other functional group, such as an ether, carbonate, carbamate or ester functional group, and wherein the aromatic moiety and/or the aliphatic moiety may optional comprise a hetero atom. In other words, an "aralkyl group" represents an alkyl or cycloalkyl group (or a heteroalkyl or heterocycloalkyl group) having an aryl group (or a heteroaryl group) as a substituent. Suitable aliphatic and aromatic moieties of the aralkyl group correspond to the alkyl, cycloalkyl and aryl groups (or heteroalkyl, heterocycloalkyl and heteroaryl groups, respectively), as defined above.

An "alkaryl group", as used herein, denotes a group having an aliphatic and an aromatic moiety, wherein the aliphatic moiety binds to the terminal alkyne functional group or any other functional group, such as an ether, carbonate, carbamate or ester functional group, and wherein the aliphatic moiety and/or the aromatic moiety may optional comprise a hetero atom. In other words, an "alkaryl group" represents an aryl group (or a heteroaryl group) having an alkyl or cycloalkyl group (or a heteroalkyl or heterocycloalkyl group) as a substituent. Suitable aliphatic and aromatic moieties of the alkaryl group correspond to the alkyl, cycloalkyl and aryl groups (or heteroalkyl, heterocycloalkyl and heteroaryl groups, respectively), as defined above.

In an embodiment, the terminal alkyne functional group of the compound C1 is any one selected from the group consisting of propargyl, butynyl and pentynyl. Propargyl may be represented by the general formula "—$CH_2$—C≡C—H", butynyl may be represented by the general formulas "—$CH_2$—$CH_2$—C≡C—H" or "—C($CH_3$)H—C≡C—H" and pentynyl may be represented by the general formulas "—$CH_2$—$CH_2$—$CH_2$—C≡C—H", "—C($CH_3$)H—$CH_2$—C≡C—H", "—$CH_2$—C($CH_3$)H—C≡C—H" or "—C($CH_3$)$_2$—C≡C—H". The linear (unbranchend) groups thereof, i.e. "—$CH_2$—C≡C—H", "—$CH_2$—$CH_2$—C≡C—H" and "—$CH_2$—$CH_2$—$CH_2$—C≡C—H" may be preferred. A terminal alkyne functional group of the compound C1 of any one selected from the group consisting of propargyl, butynyl and pentynyl has proven to be very appropriate for the purposes of the invention.

In an embodiment, the at least one compound C1 may have at least one terminal alkyne functional group and at least one functional group selected from the group consisting of a carbonate, a carbamate, an ether and an ester.

The terms "carbonate", "carbamate", "ether" and "ester", as used herein, correspond to the generally accepted meanings thereof. A carbonate may be represented by the general formula "—O(CO)O—", a carbamate may be represented by the general formulas "—(NR)(CO)O—" or "—O(CO)(NR)—" (wherein R may—independently from each other—in particular represent a hydrogen atom, an alkyl group or any other moiety as mentioned above), an ether may be represented by the general formula "—O—" and an ester may be represented by the general formula "—(CO)O—" or "—O(CO)—".

These functional groups may provide an appropriate adjustment of physiological properties of a product (such as a polymer or an article comprising or formed the polymer) obtained after the thiol-yne-alkene reaction, for instance by a printing method, in a human or animal body, such as when used as a medical or biomedical device. For instance, an ether functional group is hardly hydrolysable under a physiological environment and consequently a product obtained from a resin composition wherein the at least one component C1 comprises an ether functional group is substantially non-biodegradable and is therefore in particular suitable as a dental product, such as a dental prosthesis. On the other hand, a carbamate functional group and in particular a carbonate functional group and an ester functional group can be more easily hydrolysed (for instance enzymatically) under a physiological environment and consequently a product obtained from a resin composition wherein the at least one component C1 comprises a carbamate functional group, a carbonate functional group and/or an ester functional group is substantially biodegradable and is therefore in particular suitable as an implant, a bone substitute and/or a tissue substitute, which are often intended to gradually degrade and become substituted by natural, physiological material. It might also be advantageous that the product is at least partially biodegradable and at least partially non-biodegradable, for instance if a certain persistent mechanical support is desired, or that a part of the product biodegrades relatively fast whereas a part of the product biodegrades relatively slowly, which might be in particular advantageous when using the product as an implant, a bone substitute and/or a tissue substitute. Thus, also combinations of ether, carbamate, carbonate and/or ester functional groups, might be appropriate according to specific needs. Other functional groups being more or less hydrolysable/cleavable under physiological conditions may be contained in the compound C1, but also in the compound C2 and/or the compound C3.

In an embodiment, the at least one compound C1 may comprise a compound having a functional group selected from the group consisting of a propargyl carbonate, a propargyl carbamate, a propargyl ether, a propargyl ester, a butynyl carbonate, a butynyl carbamate, a butynyl ether, a butynyl ester, a pentynyl carbonate, a pentynyl carbamate, a pentynyl ether, and a pentynyl ester.

In an embodiment, the at least one compound C1 has one terminal alkyne functional group. Monofunctional alkyne monomers are typically liquids having a relatively low viscosity. If such monofunctional alkyne monomers are contained in the resin composition, the resin composition is also typically liquid having a relatively low viscosity. Such low viscous liquids are in particular suitable as an ink for an ink-jet printing method where highly viscous inks might be difficult to eject from the ink-jet nozzle. It should be noted that due the presence of a carbon-carbon triple bond in the yne monomer, one monofunctional alkyne monomer can react with two thiol functional groups in a thiol-yne-alkene reaction so that the polymerization reaction can proceed (does not terminate) even if only one functional alkine group is present in the yne monomer.

In an embodiment, the at least one compound C1 has at least two terminal alkyne functional groups, such as 2, 3, 4, 5, 6, 7, 8, 9, 10, 11, 12, 13, 14, 15, 16, 17, 18, 19, 20 or more terminal alkyne functional group. Such compounds C1 may be in particular advantageous when a low viscosity of the resin composition is not required and/or where a particular strong polymeric network with a large variety of cross-linkages is desired.

Appropriate examples of the at least one compound C1 include for instance the following compounds:

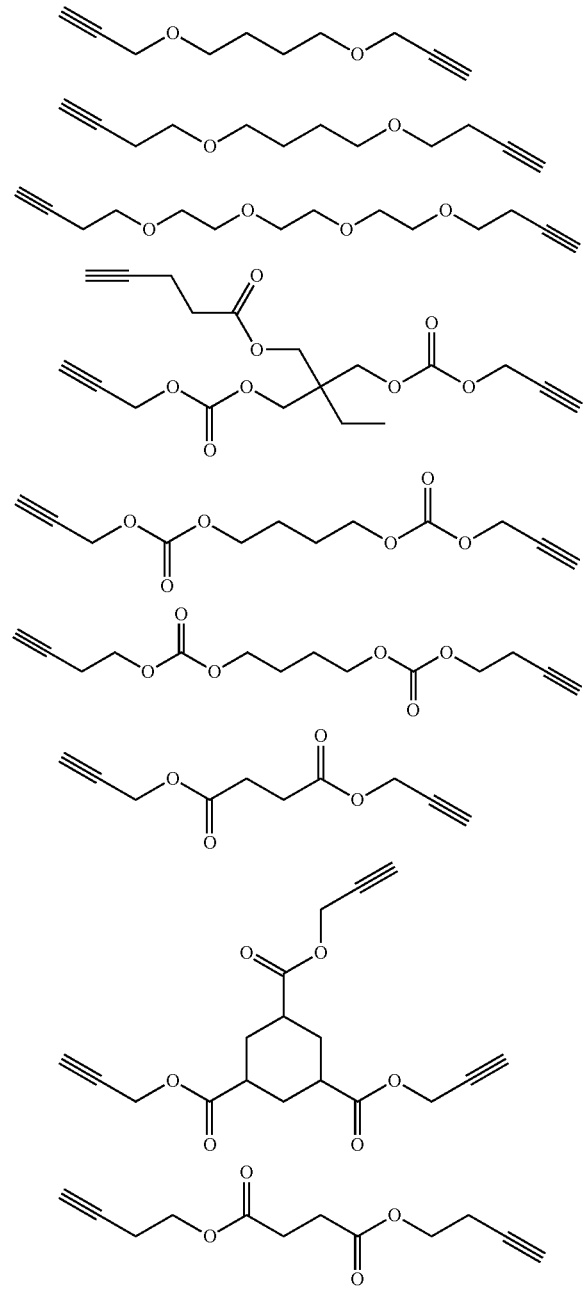

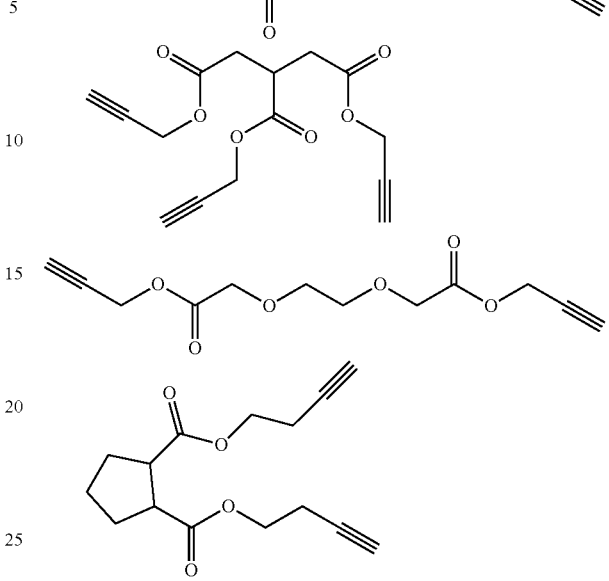

In addition, di(but-3-yn-1-yl) carbonate, di(prop-2-yn-1-yl) carbonate and di(but-3-yn-1-yl) (2,2,4-trimethylhexane-1,6-diyl)dicarbamate represents a further appropriate example of the at least one compound C1.

The compounds C1 as defined herein can be prepared by well-established organic synthesis methods using commercially available starting materials.

For example, a compound having at least one terminal alkyne functional group and at least one carbonate functional group can be prepared as shown below by way of specific examples. It should be noted that these specific examples are only for illustrative purposes and should not be construed limiting in any way.

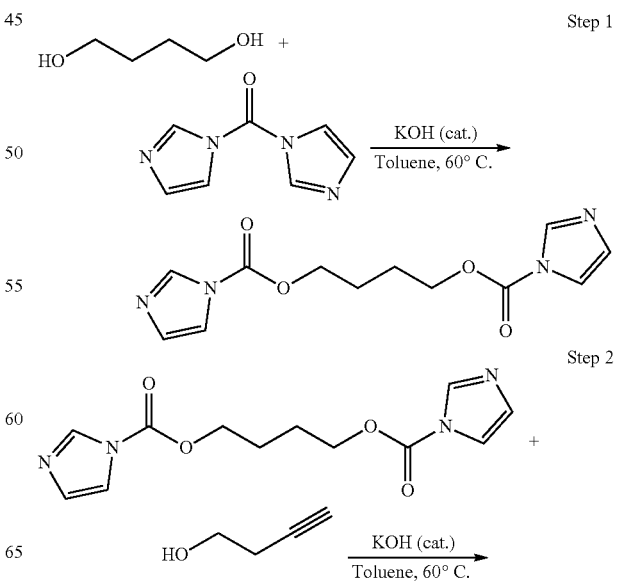

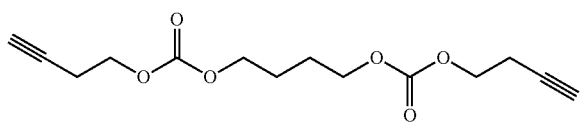

As an alternative approach to the above two-step method, the following one-step method for synthesizing compounds having at least one terminal alkyne functional group and at least one carbonate functional group is illustrated below:

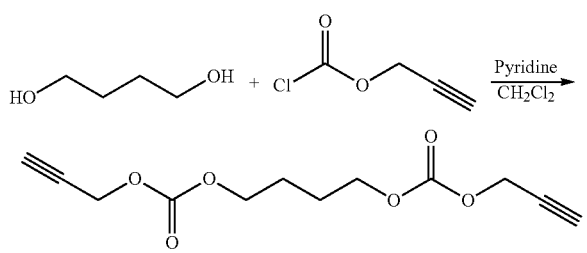

As a further example, a compound having at least one terminal alkyne functional group and at least one ether functional group can be prepared by means of Williamson ether synthesis, as illustrated below:

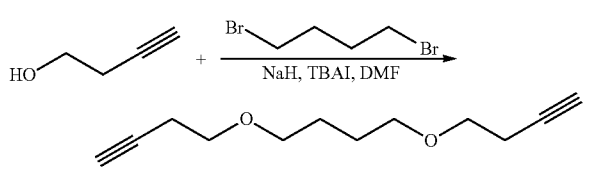

As a still further example, a compound having at least one terminal alkyne functional group and at least one ester functional group can be prepared as shown below by way of specific examples. One approach for synthesizing compounds having at least one terminal alkyne functional group and at least one ester functional group according to Schotten-Baumann esterification synthesis is illustrated below:

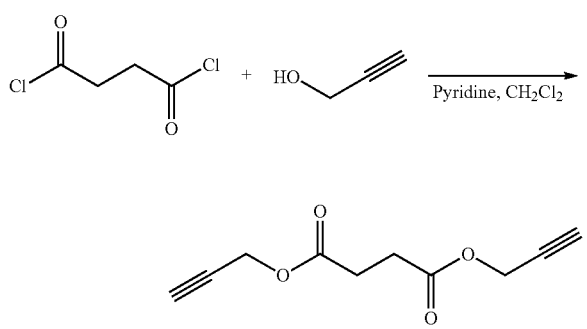

As an alternative approach to the above method, the following method for synthesizing compounds having at least one terminal alkyne functional group and at least one ester functional group by means of Steglich esterification synthesis is illustrated below:

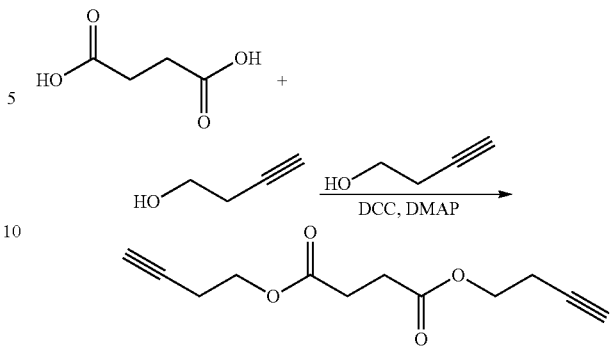

As a further example, a compound having at least one terminal alkyne functional group and at least one ester functional group can be prepared by means of Fischer-Speier esterification synthesis, as illustrated below:

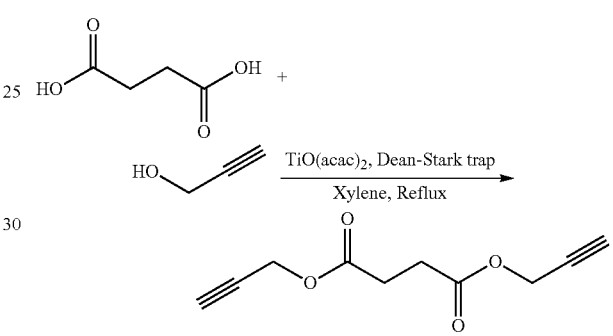

The compound C2 has at least two thiol functional groups.

The term "thiol functional group", as used herein and as commonly understood by a person skilled in the art, represents a functional group represented by the general formula "—SH" which may also be present in protected form represented for instance by the general formula "—SZ", wherein "Z" represents a protection group for "—SH", i.e. a thiol protection group.

In an embodiment, at least one of the thiol functional groups comprises a thiol protecting group. In other words, at least one of the thiol functional groups may be present in protected form or at least one of the thiol functional groups may be represented by the general formula "—SZ", wherein "Z" represents a protection group for "—SH", i.e. a thiol protection group. The thiol protection group may be in particular selected from the group consisting of an acyl group, a silyl group and a siloxyl group. In case of an acyl thiol protection group, the thiol functional group in particular represents a thioester. In case of a silyl thiol protection group, the thiol functional group in particular represents a silyl thioether. In case of a siloxyl thiol protection group, the thiol functional group in particular represents a silyl thioester.

Suitable examples for an acyl thiol protection group include formyl and acetyl. Suitable examples for a silyl thiol protection group include trimethylsilyl, triethylsilyl, tert-butyldimethylsilyl, tert-hexylsilyl, trihexylsilyl and tripropylsilyl. Suitable examples for a siloxyl thiol protection group include trimethylsiloxyl, triethylsiloxyl, tert-butyldimethylsiloxyl, tert-hexylsiloxyl, trihexylsiloxyl and tripropylsiloxyl.

Appropriate deprotection (removal of the protecting group) should then be carried out, as it is well known to a person skilled in the art, prior to the use of the resin composition, for instance in a printing method or in any other intended use thereof where the thiol functional group is intended to take part in a thiol-yne-alkene reaction. For instance, in case of a silyl thiol protection group (a silyl thioether), deprotection may be carried out by reaction with a photoacid, i.e. a compound that generates an acid upon irradiation with electromagnetic radiation. Likewise, in case of an acyl or a siloxyl thiol protection group (a thioester or a silyl thioester), deprotection may be carried out by reaction with a photobase, i.e. a compound that generates a base upon irradiation with electromagnetic radiation.

Accordingly, the resin composition may further comprise at least one photoacid and/or at least one photobase. In particular, in case of a silyl thiol protection group (a silyl thioether), the resin composition may further comprise at least one photoacid and in case of an acyl or a siloxyl thiol protection group (a thioester or a silylthioester), the resin composition may further comprise at least one photobase.

Suitable examples for a photoacid (photoacid generator, PAG) include

Ionic photoacid generators, in particular
   Onium salts, such as onium salts of aryldiazonium, diaryliodonium (e.g. Cyracure UVI-6976 available from The Dow Chemical Company, Esacure 1064 available from Lamberti SpA, QL Cure 211 available from CHANGZHOU TRONLY NEW ELECTRONIC MATERIALS CO., LTD), triarylsulfonium (e.g. Omnicat 440 available from IGM Resins B.V., Irgacure 250 available from BASF SE, Rhodorsil 207 available from Rhodia), triarylselenonium or triarylphosphonium salts that contain complex halides such as $BF_4^-$, $SbF_6^-$, $AsF_6^-$, $B(C_6F_5)_4^-$ or $PF_6^-$ as counter ions,
   Iron arene complexes (e.g. Irgacure 261 available from BASF SE) that contain complex halides such as $BF_4^-$, $SbF_6^-$, $AsF_6^-$, $B(C_6F_5)_4^-$ or $PF_6^-$ as counter ions,
   Dialkylphenacyl sulfonium salts that contain complex halides such as $BF_4^-$, $SbF_6^-$, $AsF_6^-$, $B(C_6F_5)_4^-$ or $PF_6^-$ as counter ions Non-ionic photoacid generators, in particular
   2-Nitrobenzylester of carboxylic acids
   2-Nitrobenzylester of sulfonic acids
   Sulfones compounds which generate sulfinic acid upon UV irradiation
   Triarylphosphates
   N-Hydroxyimide sulfonates (e.g. N-Hydroxy-5-norbornene-2,3-dicarboximide perfluoro-1-butanesulfonate)
   Sulfonic acid esters of phenol
   Diazonaphthoquinones
   Imino sulfonates
   Trichloromethyl-1,3,5-triazines (e.g. 2-(4-Methoxystyryl)-4,6-bis(trichloromethyl)-1,3,5-triazine)

and/or mixtures of any one of the foregoing.

Suitable examples for a photobase (photobase generator, PBG) include
   Carbamates (e.g. m-nitrophenyl, 3,5-dimethoxybenzyl, 1-methyl-1-(3,5-dimethoxyphenyl)ethyl, α-methylnitropiperonyl, o-nitrobenzyl, 3,4-dimethoxy-6-nitrobenzyl, phenyl(o-nitrophenyl)methyl, 2-(2-nitrophenyl) ethyl, 6-nitroveratryl, 4-methoxyphenacyl, 3'5'-dimethoxybenzoin carbamates)
   o-Acyloximes
   Ammonium salts
   Sulfoamides
   Formamides
   Nifedipines
   Amineimides
   α-Aminoketons
   o-Carbamoyloximes and/or mixtures of any one of the foregoing.

In an embodiment, the at least one compound C2 may be represented by the following general formula (XIII):

$$X + L - S - Z]_z \quad (XIII)$$

wherein
   z represents an integer of from 2 to 1000;
   Z represents—independently from each other on each occurrence—hydrogen or a thiol protecting group;
   L represents—independently from each other on each occurrence—a single bond or a divalent group selected from the group consisting of a linear or branched, saturated or unsaturated, substituted or unsubstituted alkylene group; a linear or branched, saturated or unsaturated, substituted or unsubstituted heteroalkylene group; a saturated or unsaturated, substituted or unsubstituted cycloalkylene group; a saturated or unsaturated, substituted or unsubstituted heterocycloalkylene group; a substituted or unsubstituted arylene group; a substituted or unsubstituted heteroarylene group; a linear or branched, substituted or unsubstituted aralkylene group; a linear or branched, substituted or unsubstituted alkarylene group; or a silicium containing divalent group; and
   X represents a z-valent group selected from the group consisting of a linear or branched, saturated or unsaturated, substituted or unsubstituted alkyl group; a linear or branched, saturated or unsaturated, substituted or unsubstituted heteroalkyl group; a saturated or unsaturated, substituted or unsubstituted cycloalkyl group; a saturated or unsaturated, substituted or unsubstituted heterocycloalkyl group; a substituted or unsubstituted aryl group; a substituted or unsubstituted heteroaryl group; a linear or branched, substituted or unsubstituted aralkyl group; a linear or branched, substituted or unsubstituted alkaryl group; or a silicium containing z-valent group.

In the general formula (XIII), z may in particular represent an integer of from 2 to 1000, with a lower range limit of for instance 2, 3, 4, 5, 6, 7, 8, 9, 10, 11, 12, 13, 14, 15, 16, 17, 18, 19, 20, 25, 30, 35, 40, 45, 50 and/or with an upper range limit of for instance 1000, 900, 800, 750, 700, 650, 600, 550, 500, 450, 400, 350, 300, 275, 250, 225, 200, 190, 180, 170, 160, 150, 140, 130, 125, 120, 115, 110, 105, 100, 95, 90, 85, 80, 75, 70, 65, 60, 55, 50, 45, 40, 38, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, including any single combination of lower and upper range limit values.

The definitions of the terms "linear", "branched", "saturated", "unsaturated", "unsubstituted" and "substituted" may in particular correspond to the above given definitions. Similarly, the definitions and/or suitable examples of the terms "alkylene group", "heteroalkylene group", "cycloalkylene group", "heterocycloalkylene group", "arylene group", "heteroarylene group", "aralkylene group" and "alkarylene group", respectively, may in particular correspond to the above given definitions and/or suitable examples of the terms "alkyl group", "heteroalkyl group", "cycloalkyl group", "heterocycloalkyl group", "aryl group", "heteroaryl group", "aralkyl group" and "alkaryl group", respectively, except that the groups represented by L are divalent (bivalent) groups, as also indicated by their suffix "-ene". Likewise, the definitions and/or suitable examples of the terms "alkyl group", "heteroalkyl group", "cycloalkyl group", "heterocycloalkyl group", "aryl group", "heteroaryl group", "aralkyl group" and "alkaryl group" represented by X may in particular correspond to the above given definitions, except that the groups represented by X are z-valent groups.

The "silicium containing divalent group" and/or the "silicium containing z-valent group" may in particular include groups containing one or more silicium (Si) atoms and optionally further one or more of, for instance, C, O, N, P and/or H atoms. Suitable examples thereof include an Si atom, —[(Si-alkyl)$_z$]— (such as —[(Si—CH$_2$)$_z$]—), —[(Si—O)$_z$]— and —[(Si—N)$_z$]—.

In an embodiment, Z may represent—independently from each other on each occurrence—hydrogen or a thiol protection group selected from the group consisting of an acyl group, a silyl group and a siloxal group.

In an embodiment, L may—independently from each other on each occurrence—represent a single bond or a divalent group selected from the group consisting of a linear or branched, saturated or unsaturated alkylene group having from 1 to 18 carbon atoms and optionally substituted with one or more hydroxyl groups; —(CO)O—; —O(CO)—; a linear or branched, saturated or unsaturated, divalent alkyl ester group having from 1 to 18 carbon atoms; a linear or branched, saturated or unsaturated, substituted or unsubstituted acylene group having from 1 to 20 carbon atoms; a linear or branched, substituted or unsubstituted alkoxylene group having from 1 to 8 carbon atoms; a saturated or unsaturated, substituted or unsubstituted cycloalkylene group having from 3 to 12 carbon atoms; a substituted or unsubstituted arylene group having from 6 to 16 carbon atoms; or a linear or branched, saturated or unsaturated alkylene group having from 2 to carbon atoms and interspersed with one or more of oxygen, sulfur, nitrogen, phosphorus, a substituted or unsubstituted imine group, —(CO)—, —O(CO)—, —(CO)O—, —O(CO)O—, —(NR$_{10}$)(CO)O— and/or —O(CO)(NR$_{10}$)—, with R$_{10}$ being as defined above.

In an embodiment, X may represent a z-valent group selected from the group consisting of a linear or branched, saturated or unsaturated alkyl group having from 1 to 18 carbon atoms and optionally substituted with one or more hydroxyl groups; a linear or branched, saturated or unsaturated, z-valent alkyl ester group having from 1 to 18 carbon atoms; a linear or branched, saturated or unsaturated, substituted or unsubstituted acyl group having from 1 to 20 carbon atoms; a linear or branched, substituted or unsubstituted alkoxy group having from 1 to 8 carbon atoms; a saturated or unsaturated, substituted or unsubstituted cycloalkyl group having from 3 to 12 carbon atoms; a substituted or unsubstituted arylene group having from 6 to 16 carbon atoms; a linear or branched or cyclic group of any one an Si atom, —[(Si-alkyl)$_z$]— (such as —[(Si—CH$_2$)$_z$]—), —[(Si—O)$_z$]— or —[(Si—N)$_z$]—, the group being z times substituted by -L-SH; or a linear or branched, saturated or unsaturated alkyl group having from 2 to 20 carbon atoms and interspersed with one or more of oxygen, sulfur, nitrogen, phosphorus, a substituted or unsubstituted imine group, —(CO)—, —O(CO)—, —(CO)O—, —O(CO)O—, —(NR$_{10}$)(CO)O— and/or —O(CO)(NR$_{10}$)—, wherein R$^{10}$ represents—independently from each other on each occurrence—a hydrogen atom; a linear or branched, saturated or unsaturated, substituted or unsubstituted alkyl group; a linear or branched, saturated or unsaturated, substituted or unsubstituted heteroalkyl group; a saturated or unsaturated, substituted or unsubstituted cycloalkyl group; a saturated or unsaturated, substituted or unsubstituted heterocycloalkyl group; a substituted or unsubstituted aryl group; a substituted or unsubstituted heteroaryl group; a linear or branched, substituted or unsubstituted aralkyl group; or a linear or branched, substituted or unsubstituted alkaryl group.

In an embodiment, the at least one compound C2 may have at least two thiol functional groups and at least one, in particular at least two, functional group selected from the group consisting of a silane (an Si atom), a siloxane (—Si—O—), a carbonate, a carbamate, an ether and an ester, in particular at least one functional group selected from the group consisting of a carbonate, a carbamate, an ether and an ester. In particular, the number of thiol functional groups and the number of functional groups selected from the group consisting of a carbonate, a carbamate, an ether and an ester may be the same or different in the at least one compound C2. For instance, the number of thiol functional groups and/or the number of functional groups selected from the group consisting of a carbonate, a carbamate, an ether and an ester may be 2, 3, 4, 5, 6, 7, 8, 9, 10, 11, 12, 13, 14, 15, 16, 17, 18, 19, 20, 25, 30, 35, 40, 45, 50 or more and/or 1000, 900, 800, 750, 700, 650, 600, 550, 500, 450, 400, 350, 300, 275, 250, 225, 200, 190, 180, 170, 160, 150, 140, 130, 125, 120, 115, 110, 105, 100, 95, 90, 85, 80, 75, 70, 65, 60, 55, 50, 45, 40, 38, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3 or less.

In an embodiment, it might be advantageous that the at least one compound C2 comprises a carbamate functional group, a carbonate functional group and/or an ester functional group. By taking this measure, the polymer and/or the article resulting from a polymerization of the resin composition may be substantially biodegradable and may therefore be in particular suitable as an implant, a bone substitute and/or a tissue substitute, which are often intended to gradually degrade and become substituted by natural, physiological material.

Appropriate examples of the at least one compound C2 include for instance the following compounds:

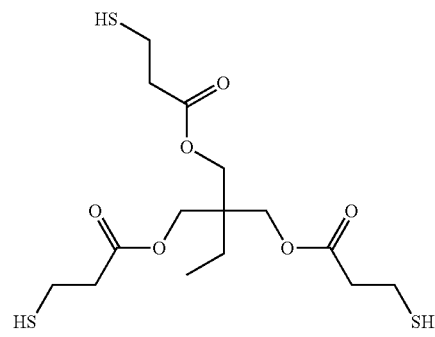 [SMILES: CCC(COC(=O)CCS)(COC(=O)CCS)COC(=O)CCS]

Trimethylolpropane tris(3-mercaptopropionate) (TMPMP)

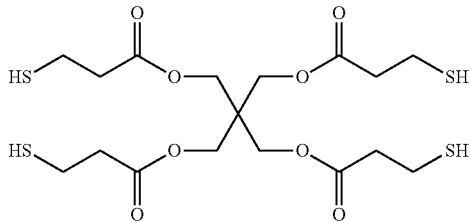 [SMILES: O=C(CCS)OCC(COC(=O)CCS)(COC(=O)CCS)COC(=O)CCS]

Pentaerythritol tetrakis(3-mercaptopropionate) (PETMP)

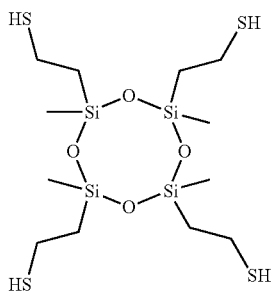

THIO-1

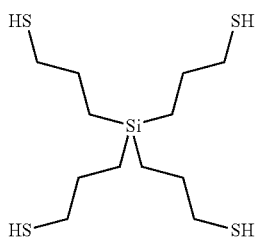

THIO-2

THIO-3

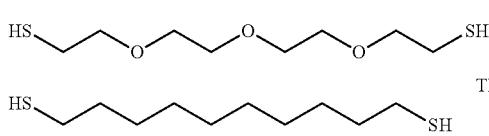

THIO-4

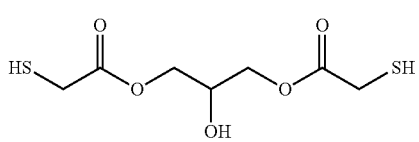

THIO-5

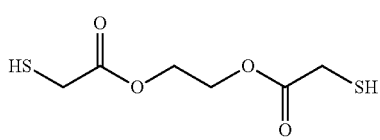

THIO-6

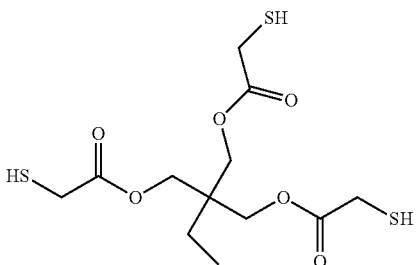

THIO-7

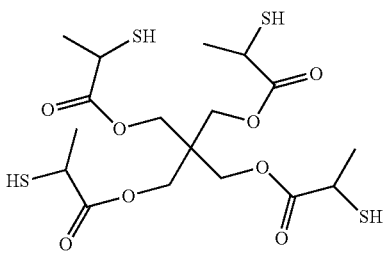

THIO-8

Further appropriate examples of the at least one compound C2 are shown on pages 23 and 24 of WO 2013/052328 A1, the disclosure of which is incorporated herein by reference.

The compound C3 has at least one carbon-carbon double bond. In an embodiment, one of the carbon atoms of the carbon-carbon double bond binds to a hydrogen atom. In an embodiment, the compound C3 has at least one terminal alkene functional group (or at least one terminal carbon-carbon double bond).

In an embodiment, the at least one compound C3 having at least one carbon-carbon double bond may have at least one functional group selected from the group consisting of a vinyl functional group, an allyl functional group, an acrylate functional group and a methacrylate functional group. In other words, the at least one carbon-carbon double bond may in particular be part of a vinyl functional group, an allyl functional group, an acrylate functional group and/or a methacrylate functional group. These functional groups provide for an alkene monomer, which may undergo thiol-yne-alkene reaction in a particular efficient and fast manner and under very high monomeric conversion such that the resulting polymer may be substantially free of any residuals monomers, thereby strongly reducing or substantially avoiding any negative effects caused by remaining monomers, such as cytotoxicity issues. In particular, the at least one compound C3 having at least one carbon-carbon double bond may have at least one functional group selected from the group consisting of an allyl functional group, an acrylate functional group and a methacrylate functional group.

The terms "vinyl", "allyl", "acrylate" and "methacrylate" as used herein, correspond to the generally accepted meanings thereof. A vinyl may be represented by the general formula "H$_2$C═CH—", an allyl may be represented by the general formula "H$_2$C═CH—CH$_2$—", an acrylate may be represented by the general formula "H$_2$C═CH—C(═O)—" and a methacrylate may be represented by the general formula "H$_2$C═C(CH$_3$)—C(═O)—". A "(meth)acrylate" may encompass an acrylate and/or a methacrylate.

In an embodiment, the at least one compound C3 having at least one carbon-carbon double bond may have at least one vinyl functional group and/or allyl functional group.

Suitable examples thereof include diallylpyrocarbonate; diallyl (2,2,4-trimethylhexane-1,6-diyl)dicarbamate; allyl acetate; allyl benzyl ether; allyl butyl ether; allyl cyanoacetate; allyl ether; allyl ethyl ether; allyl methyl carbonate; 2-allyloxybenzaldehyde; 2-allyloxyethanol; 4-allyloxy-2-hydroxybenzophenone; 3-allyloxy-1,2-propanediol; allyl phenyl ether; allylphosphonic acid monoammonium salt; 2,2'-diallylbisphenol; 2,2'-diallyl bisphenol A diacetate ether; diallyl carbonate; diallyl maleate; diethyl allylmalonate; 5-methyl-5-allyloxycarbonyl-1,3-dioxan-2-one; pentaerythritol allyl ether; 2,4,6-triallyloxy-1,3,5-triazine; 1,3,5-triallyl-1,3,5-triazine-2,4,6(1H,3H,5H)-trione; trimethylolpropane allyl ether; trimethylolpropane diallyl ether; 1,4-butanediol divinyl ether; 1,4-butanediol vinyl ether; butyl vinyl ether; tert-butyl vinyl ether; 2-chloroethyl vinyl ether; 1,4-cyclohexanedimethanol divinyl ether; 1,4-cyclohexanedimethanol vinyl ether; cyclohexyl vinyl ether; di(ethylene glycol) divinyl ether; di(ethylene glycol) vinyl ether; diethyl vinyl orthoformate; dodecyl vinyl ether; ethylene glycol vinyl ether; 2-ethylhexyl vinyl ether; ethyl vinyl ether; isobutyl vinyl ether; phenyl vinyl ether; propyl vinyl ether; vinyl acetate; vinyl benzoate; vinyl cinnamate; vinyl decanoate; vinyl neodecanoate; vinyl neononanoate; vinyl pivalate; vinyl propionate; vinyl stearate; hexandiol divinylester; hexandiol divinylcarbonate; butandiol divinylcarbonate; N-vinyl-pyrrolidone; N-vinyl-caprolactam; N-vinyl-imidazole; N-vinyl-N-methylacetamide; 1,4-butanediol divinyl ether; diethyleneglycol divinyl ether; triethyleneglycol divinyl ether; 1,4-cyclohexanedimethanol divinyl ether; hydroxybutyl vinyl ether; 1,4-cyclohexanedimethanol mono vinyl ether; 1,2,4-trivinylcyclohexane; and diallyl (2,2,4-trimethylhexane-1,6-diyl)dicarbamate.

In an embodiment, the at least one compound C3 having at least one carbon-carbon double bond may have at least one (meth)acrylate functional group. Suitable examples thereof include 1,4-butanediol diacrylate; 1,4-butanediol dimethacrylate; isobutyl methacrylate; 1,3-butylene glycol diacrylate; di-trimethylolpropane tetraacrylate; hexanediol diacrylate; ethoxy (3) cyclohexanol dimethanol diacrylate; 2-(2-ethoxyethoxy) ethyl acrylate; dipentaerythritol pentaacrylate; tripropylene glycol diacrylate; ethoxy (3) cyclohexanol dimethanol diacrylate; 2-phenoxy ethyl acrylate; propoxylated (3) trimethylolpropane triacrylate; dipropylene glycol diacrylate; propoxylated (3) cyclohexanol dimethanol diacrylate; cyclic trimethylolpropane formal acrylate; ethoxylated (5) pentaerythritol tetraacrylate; ethoxy (3) hexanediol diacrylate; ethoxy (3) phenoxy ethyl acrylate; ethoxy (6) trimethylolpropane triacrylate; ethoxy (5) hexanediol diacrylate; propoxylated (6) trimethylolpropane triacrylate; propoxylated (3) hexanediol diacrylate; propoxylated (3) glyceryl triacrylate; propoxylated (2) neopentyl glycol diacrylate; 2(2-ethoxyethoxy)ethyl acrylate; isodecyl acrylate; octyl/decyl acrylate; lauryl acrylate; tridecyl acrylate; caprolactone acrylate; diethylene glycol butyl ether acrylate; isobornyl acrylate; tetrahydrofurfuryl acrylate; cyclic trimethylolpropane formal acrylate; isophoryl acrylate; 2-phenoxyethyl acrylate; ethoxylated (4) phenol acrylate; ethoxylated (4) nonyl phenol acrylate; hexanediol diacrylate; tricyclodecane dimethanol diacrylate; dioxane glycol diacrylate; dipropylene glycol diacrylate; tripropylene glycol diacrylate; polyethylene glycol (200) diacrylate; ethoxylated bisphenol A diacrylate; propoxylated (2) neopentyl glycol diacrylate; trimethylolpropane triacrylate; propoxylated (3) trimethylolpropane triacrylate; ethoxylated (3) trimethylolpropane triacrylate; propoxylated glycerol triacrylate; tris(2-hydroxylethyl)isocyanurate triacrylate; dipentaerythritol penta/hexa acrylate; alkoxylated pentaerythritol tetraacrylate; di(trimethylol)propane tetraacrylate; epoxy acrylate; urethane acrylate; polyester acrylate; 4-acetoxyphenethyl acrylate; -acryloylmorpholine; (4-benzoyl-3-hydroxyphenoxy)ethyl acrylate; benzyl 2-propylacrylate; butyl acrylate; tert-butyl acrylate; 2-carboxyethyl acrylate; 2-carboxyethyl acrylate; 2-chloroethyl acrylate; 2-(diethylamino)ethyl acrylate; di(ethylene glycol) ethyl ether acrylate; 2-(dimethylamino)ethyl acrylate; 3-(dimethylamino)propyl acrylate; dipentaerythritol penta-/hexa-acrylate; ethyl acrylate; ethyl 2-(bromomethyl)acrylate; ethyl cis-(R-cyano)acrylate; ethylene glycol dicyclopentenyl ether acrylate; ethylene glycol methyl ether acrylate; ethylene glycol phenyl ether acrylate; ethyl 2-ethylacrylate; 2-ethylhexyl acrylate; ethyl 2-propylacrylate; ethyl 2-(trimethylsilylmethyl)acrylate; hexyl acrylate; 4-hydroxybutyl acrylate; 2-hydroxyethyl acrylate; 2-hydroxy-3-phenoxypropyl acrylate; hydroxypropyl acrylate; isobornyl acrylate; isobutyl acrylate; isodecyl acrylate; isooctyl acrylate; lauryl acrylate; methyl 2-acetamidoacrylate; methyl acrylate; methyl 2-(bromomethyl)acrylate; methyl 2-(chloromethyl)acrylate; methyl 3-hydroxy-2-methylenebutyrate; methyl 2-(trifluoromethyl)acrylate; octadecyl acrylate; pentabromobenzyl acrylate; pentabromophenyl acrylate; pentafluorophenyl acrylate; poly(ethylene glycol) diacrylate; poly (ethylene glycol) methyl ether acrylate; N-propylacrylamide; soybean oil epoxidized acrylate; tetrahydrofurfuryl acrylate; 2-tetrahydropyranyl acrylate; 3-(trimethoxysilyl)propyl acrylate; 3;5;5-trimethylhexyl acrylate; 10-undecenyl acrylate; urethane acrylate methacrylate; allyl methacrylate; 2-[3-(2H-benzotriazol-2-yl)-4-hydroxyphenyl]ethyl methacrylate; benzyl methacrylate; bis (2-methacryloyl)oxyethyl disulfide; butyl methacrylate, tert-butyl methacrylate, 9H-carbazole-9-ethylmethacrylate; cyclohexyl methacrylate; 1,10-decamethylene glycol dimethacrylate; 2-(diethylamino)ethyl methacrylate; diethylene glycol butyl ether methacrylate; di(ethylene glycol) methyl ether methacrylate; 2-(diisopropylamino)ethyl methacrylate; 2-(dimethylamino)ethyl methacrylate; 2-ethoxyethyl methacrylate; ethylene glycol dicyclopentenyl ether methacrylate; ethylene glycol methyl ether methacrylate; ethylene glycol phenyl ether methacrylate; 2-ethylhexyl methacrylate; ethyl methacrylate; furfuryl methacrylate; glycidyl methacrylate; glycosyloxyethyl methacrylate; hexyl methacrylate; hydroxybutyl methacrylate, 2-hydroxyethyl methacrylate; 2-hydroxyethyl methacrylate; hydroxypropyl methacrylate; 2-hydroxypropyl 2-(methacryloyloxy)ethyl phthalate; 2-hydroxy-3-{3-[2,4,6,8-tetramethyl-4,6,8-tris (propyl glycidyl ether)-2-cyclotetrasiloxanyl] propoxy}propyl methacrylate; isobornyl methacrylate; isobutyl methacrylate; 2-isocyanatoethyl methacrylate; isodecyl methacrylate; lauryl methacrylate; methyl methacrylate; 2-(methylthio)ethyl methacrylate; mono-2-(methacryloyloxy)ethyl maleate; mono-2-(methacryloyloxy)ethyl succinate; 2-N-morpholinoethyl methacrylate; 1-naphthyl methacrylate; 1,4-phenylene dimethacrylate, phenyl methacrylate; phosphoric acid 2-hydroxyethyl methacrylate ester; 1-pyrenemethyl methacrylate; pyromellitic dianhydrate dimethacrylate; tetrahydrofurfuryl methacrylate; triethylene glycol methyl ether methacrylate; 3,3,5-Trimethylcyclohexyl methacrylate, urethane acrylate methacrylate; urethane epoxy methacrylate; vinyl methacrylate; and urethane dimethacrylate.

In an embodiment, the at least one compound C3 may have at least one carbon-carbon double bond and at least one functional group selected from the group consisting of a carbonate, a carbamate, an ether and an ester. These functional groups may provide an appropriate adjustment of physiological properties of a product (such as a polymer or an article comprising or formed the polymer) obtained after the thiol-yne-alkene reaction, similar to the explanations given above in the context of compound C1.

In an embodiment, the at least one compound C3 has at least two carbon-carbon double bonds, in particular at least two terminal alkene functional group, such as 2, 3, 4, 5, 6, 7, 8, 9, 10, 11, 12, 13, 14, 15, 16, 17, 18, 19, 20 or more carbon-carbon double bonds (in particular terminal alkene functional groups, in particular functional groups selected from the group consisting of an allyl functional group, an acrylate functional group and a methacrylate functional group).

In an embodiment, the ratio of the number of terminal alkyne functional groups to the number of thiol functional groups to the number of carbon-carbon double bonds (in particular terminal alkene functional groups) may be adjusted such that the number of residual (after completion of the thiol-yne-alkene reaction) reactive groups and the number of residual (after completion of the thiol-yne-alkene reaction) monomers in the polymer formed are minimized, which may be advantageous in particular when the polymer (or an article comprising or formed from the monomer) is used in medical or biomedical appliances.

In an embodiment, the ratio of the number of terminal alkyne functional groups to the number of thiol functional groups to the number of carbon-carbon double bonds (in particular terminal alkene functional groups) may be adjusted such that some thiol functional groups may remain in the polymer formed after completion of the thiol-yne-alkene reaction, in particular on the surface of the polymer or of an article comprising or formed from the polymer. Thereby, a surface-modified polymer or article may be obtained. In particular, such remaining or residual thiol functional groups may serve as an anchor or docking site (binding site) capable for coupling the polymer or the article with an additive, such as an organic filler (e.g. heparin), and/or with a coating agent, such as an antimicrobial agent, for instance a quaternary amine. The binding (coupling) of the remaining or residual thiol functional group with an additive or coating agent may be carried out for instance by means of a thiol-ene reaction, such as a thiol-Michael addition, typically catalyzed under basic conditions. The binding (coupling) of the remaining or residual thiol functional group with a coating agent may also involve the formation of disulfide bonds (disulfide bridges), in particular in case of a protein or a peptide to be coupled with the polymer or article. Thereby, the polymer or article can be imparted with additional physiologically beneficial properties, for instance with anticoagulant properties in case of heparin, and/or at least a part of the surface of the polymer or article may be provided with a (nano)coating, in particular an antimicrobial coating.

The at least one compound C1 may be contained in the resin composition in an amount of from 5 to 80 wt.-%, in particular from 10 to 75 wt.-%, in particular from 15 to 70 wt.-%, in particular from 20 to 65 wt.-%, such as from 20 to 60 wt.-%, from 25 to 55 wt.-%, from 30 to 50 wt.-%, from 35 to 45 wt.-%, or from to 40 wt.-%.

The at least one compound C2 may be contained in the resin composition in an amount of from 5 to 80 wt.-%, in particular from 10 to 75 wt.-%, in particular from 15 to 70 wt.-%, in particular from 20 to 65 wt.-%, such as from 20 to 60 wt.-%, from 25 to 55 wt.-%, from 30 to 50 wt.-%, from 35 to 45 wt.-%, or from to 40 wt.-%.

The at least one compound C3 may be contained in the resin composition in an amount of from 10 to 90 wt.-%, in particular from 15 to 85 wt.-%, in particular from 20 to 80 wt.-%, in particular from 25 to 70 wt.-%, such as from 20 to 60 wt.-%, from 25 to 55 wt.-%, from 30 to 50 wt.-%, from 35 to 45 wt.-%, or from to 40 wt.-%.

In an embodiment, the at least one compound C3 is contained in a larger amount than the at least one compound C1 and/or the at least one compound C2.

In an embodiment, the ratio of the at least one compound C1/the at least one compound C2/the at least one compound C3 may be 5-40/5-60/10-90 wt.-%, in particular 10-30/10-50/20-80 wt.-%, when the total of the at least one compound C1, the at least one compound C2 and the at least one compound C3 is considered as 100 wt.-%.

In an embodiment, the number of terminal alkyne functional groups (in particular from compound C1) to the number of thiol functional groups (in particular from compound C2) to the number of carbon-carbon double bonds (in particular from compound C3) may be for instance about 1:3:3, 1:2:4, 1:2:12, 2:3:3 or 2:2:4.

The inventors have found that with increasing ratio of the at least one compound C2 (comprising thiol groups) compared to the at least one compound C1 and/or the at least one compound C3 (i.e. if a relatively large amount of thiol groups-containing compounds C2 is used compared to the other two compounds C1 and C3), the network density of the resulting polymer decreases, while the homogeneity of the polymer and its biodegradability increases.

The resin composition further comprises at least one photoinitiator. The presence of at least one photoinitiator in the resin composition may facilitate the initiation of the reaction between the yne component, the thiol component and the alkene component in a thiol-yne-alkene reaction. Thus, the presence of at least one photoinitiator may increase the polymerization speed (velocity) and/or reduce the curing time. As a consequence, the presence of at least one photoinitiator is in particular advantageous when the resin composition is used as or in an ink for a printing method, in particular a three-dimensional printing method where typically the object to be printed is formed layer by layer requiring the previous layer to be substantially hardened or cured before forming the subsequent layer. In addition by using a photoinitiator, the thiol-yne-alkene reaction can be selectively controlled, in particular in terms of a specific location or area of or within the resin composition where the polymerization is supposed to be initiated/promoted, as desired, for instance by directing an appropriate energy-carrying activation beam to the specific location or area, thereby enabling the formation of specific structures with high resolution as a result of a printing method.

The term "photoinitiator", as used herein, in particular denotes a compound which can be activated by an energy-carrying activation beam (such as electromagnetic radiation), for instance upon irradiation therewith. Upon activation by an energy-carrying beam, the photoinitiator may be in particular converted into a radical thereof. Thus, the photoinitiator may be in particular a radical generating photoinitiator.

The photoinitiator may be in particular a type I photoinitiator or a type II photoinitiator.

The photoinitiator may be in particular an ultraviolet-active photoinitiator and/or a visible light-active photoinitiator. In other words, the photoinitiator may be in particular a compound that can be activated by electromagnetic radiation in the ultraviolet wavelength region (such as the wavelength range of from 10 to 380 nm, in particular from 200 to 380 nm) and or by electromagnetic radiation in the wavelength region of visible light (such as the wavelength range of from 380 to 780 nm)

The photoinitiator is not particularly limited, as long as it can be activated by electromagnetic radiation to thereby initiate the thiol-yne-alkene reaction between the yne component, the thiol component and the alkene component in the resin composition.

In an embodiment, the photoinitiator may be at least one compound selected from the group consisting of a quinone compound, camphorquinone, an azide compound, an azo compound, in particular azobisisobutyronitrile (AIBN), a peroxide compound, in particular benzoyl peroxide, a disulfide compound, a bis-imidazole compound, an alkyl halogenide, an alkyl thiocyanate, a phosphinoxide compound, a substituted or unsubstituted thioxanthone, a substituted or unsubstituted benzophenone or mixtures thereof. The term "substituted" may in particular correspond to that, as defined above in, as long as the substituent does not substantially reduce the reactivity of the photoinitiator. As it is well known to a person skilled in the art, these compounds may form radicals and/or moieties having unshared valence electrons or at least one unshared electron pair upon activation by actinic energy.

Suitable examples of the photoinitiator include thioxanthen-9-one, 2-chloro-; 9H-thioxanthene-2-carboxylic acid, 9-oxo-, ethyl ester; 2,4,6-trimethylbenzophenone; 2,2-dimethoxy-2-phenyl acetophenone; 2-(dimethylamino)ethylbenzoate; 1-[4-(1,1-dimethylethyl)phenyl]-2-hydroxy-2-methylpropan-1-one; erbium oxide sulfide; 2-ethylanthraquinone; ethylbenzoylformate; 2-hydroxy-[4'-(2-hydroxypropoxy) phenyl]-2-methylpropanone; 2-hydroxy-2-methyl propiophenone; 1-hydroxycyclohexyl-phenyl-ketone; methylbenzoylformate; 4-(4-methylphenylthio)-benzophenone; 1-phenyl-1,2-propanedione-2-(O-ethoxycarbonyl)oxim; 4-phenylbenzophenone; phosphine oxide, triphenyl-; poly(oxy-1,2-ethanediyl), a-[2-(4-chlorobenzoyl)benzoyl]-w-[[2-(4-chlorobenzoyl)benzoyl]oxy]-; 4,4'-bis(methylethylamino)benzophenone; butoxyethyl-4-(dimethylamino) benzoate; d,l-camphorquinone; 1-chloro-4-propoxythioxanthone; 9,10-dibutoxyanthracene; 2,2-diethoxy acetophenone; 2,4-diethyl-9H-thioxanthen-9-on; 2,3-dihydroxy-6-(2-hydroxy-2-methyl-1-oxopropyl)-1,1,3-trimethyl-3-[4-(2-hydroxy-2-methyl-1-oxopropyl)phenyl]-1H-indene; anthraquinone, 2-ethyl-; 1H-azepine-1-propanoic acid, hexahydro-, 2,2-bis[[(1-oxo-2-propenyl)oxy] methyl]butyl ester; benzophenone, 4,4'-bis(diethylamino)-; Bis (eta5)-cyclopentadienyl)-bis(2,6-difluoro-3-[pyrrol-1-yl]-phenyl)titanium; 2,2-bis-(2-chlorophenyl)-4,4',5,5'-tetraphenyl-1,2-biimidazolyl; bis(2,6-dimethoxybenzoyl)-2,4,4-trimethylpentylphosphinoxide; benzophenone; benzophenone, 2-methyl-; benzophenone, 3-methyl-; benzophenone, 4-methyl-; ethyl-4-(dimethylamino)benzoate; 2-isopropyl thioxanthone; 4-isopropyl thioxanthone; methyl-2-benzoylbenzoate; {a-2-(phenylcarbonyl)benzoylpoly(oxyethylene)-poly[oxy(1-methylethylene)]-poly(oxyethylene)} 2-(phenylcarbonyl)benzoate; {a-4-(dimethylamino)benzoylpoly(oxyethylene)-poly[oxy(1-methylethylene)]-poly(oxyethylene)} 4-(dimethylamino) benzoate; 1,3-di({a-2-(phenylcarbonyl)benzoylpoly[oxy(1-methylethylene)]}oxy)-2,2-bis({a-2-(phenylcarbonyl)benzoylpoly[oxy(1-methylethylene)]}oxymethyl)propane; 1,3-di({-4-(dimethylamino)benzoylpoly[oxy(1-methylethylene)]}oxy)-2,2-bis({-4-(dimethylamino)benzoylpoly[oxy(1-methylethylene)]}oxymethyl) propane; 1,3-di({a-[1-chloro-9-oxo-9H-thioxanthen-4-yl)oxy]acetylpoly[oxy(1-methylethylene)]}oxy)-2,2-bis({a-[1-methylethylene)]}oxymethyl) propane; poly{1-[4-(phenyl-carbonyl)-4'-(methyldiphenylsulphide)]ethylene}; poly{1-[4-(phenylcarbonyl)phenyl]ethylene; 1-[4-(2-hydroxyethoxy)phenyl]-2-hydroxy-2-methyl-1-propanone; diphenyl-(2,4,6-trimethylbenzoyl) phosphine oxide; polymeric benzophenone derivative; polymeric thioxanthone derivative; polymeric aminobenzoate; oxy-phenylacetic acid 2-[2-hydroxy-ethoxy]-ethyl ester; oxy-phenylacetic acid 2-[2-oxo-2-phenyl-acetoxy-ethoxy]-ethyl; benzoylbenzoate, esters with branched polyols; 1-(4-[(4-Benzoylphenyl)thio]phenyl)-2-methyl-2-[(4-methylphenyl)sulfonyl]-1-propan-1-one; 2-benzyl-2-dimethylamino-4-morpholino butyrophenone; di-ester of carboxymethoxy benzophenone and polytetramethyleneglycol 250; di-ester of carboxymethoxy-benzophenone and polyethylene glycol 200; (dimethylamino)benzoate, esters with branched polyols; 2-ethylhexyl-4-dimethylamino benzoate; 2-hydroxy-1-(4-(4-(2-hydroxy-2-methylpropionyl)benzyl)phenyl-2-methyl-2-propanone; (methylamino)diethane-2,1-diylbis(4-dimethylamino amino benzoate); 2-(4-methylbenzyl)-2-dimethylamino-1-(4-morpholinophenyl)-1-butanone; oligo-[2-Hydroxy-2-methyl-1-((4-(1-methylvinyl)phenyl) propanone]; 9-oxo-9H-thioxanthene-carboxylate, esters with branched polyols; and phenyl bis(2,4,6-trimethylbenzoyl) phosphine oxide, Ivocerin, tetra acylgermanium compounds.

A particularly suitable example of a photoinitiator represents a mixture of Irgacure TPO-L and Irgacure 819. In addition, Ivocerin may be particularly advantageous in view of its high biocompatibility.

Further appropriate examples of photoinitiators are disclosed on pages 17 to 19 of WO 2013/052328 A1 and on page 13 of WO 2012/126695 A1, the disclosure of which is incorporated herein by reference.

The content of the at least one photoinitiator may be in particular from 0.1 to 20 wt.-%, such as from 0.2 to 15 wt.-%, in particular from 0.5 to 12.5 wt.-%, in particular from 1 to 10 wt.-%, in particular from 2 to 8 wt.-%, with respect to the total weight of the resin composition.

The resin composition further comprises at least one stabilizer, in particular a combination of specific stabilizers. The presence of at least one stabilizer in the resin composition improves the storage stability of the resin composition. The at least one stabilizer (or combination of several stabilizers) may in particular avoid or at least reduce a premature reaction (in particular a premature initiation and/or propagation) of a compound C1 having at least one terminal alkyne functional group and/or a compound C3 having at least one carbon-carbon double bond with a compound C2 having at least two thiol functional groups.

In an embodiment, the at least one stabilizer comprises at least one radical scavenger. The term "radical scavenger", as used herein, may in particular denote a compound which may undergo a reaction with a radical (such as a compound having an unshared electron pair), thereby eliminating or trapping the radical. In particular, the radical scavenger may include a phenolic radical scavenger or a phenolic antioxidant. Suitable examples of the radical scavenger include a hydroquinone, such as hydroquinone monomethyl ether (HQME), t-butyl catechol, pyrogallol or an ether thereof, anthralin, oxyhydrochinon, propyl gallat, lauryl gallat, butylhydroxytoluene (BHT, 2,6-di-tert-butyl-4-methylphenol), butylated hydroxyanisole (BHA, 2-tert-butyl-4-hydroxyanisole and/or 3-tert-butyl-4-hydroxyanisole), and/or di- or trihydroxybenzaldehydes, in particular 2,4-dihydroxybenzaldehyde (2,4-DHB), 3,4-dihydroxybenzaldehyde (3,4-DHB), 3,5-dihydroxybenzaldehyde (3,5-DHB), 2,5-dihydroxybenzaldehyde (2,5-DHB), 2,3-dihydroxybenzaldehyde (2,3-DHB) and/or 2,3,4- trihydroxybenzaldehyde (2,3,4-THB). Particular suitable examples of the radical scavenger include pyrogallol, anthralin, oxyhydrochinon, propyl gallat, BHT and the di- or trihydroxybenzaldehydes exemplified above.

In an embodiment, the at least one stabilizer comprises at least one phosphorous containing compound, in particular at least one phosphonic acid and/or at least one phosphoric acid and/or a derivative (in particular an ester) thereof. Such stabilizer compounds may in particular suitable for suppressing a (premature) thiol-Michael reaction. Suitable examples of a phosphonic acid include alkylphosphonic acid, vinylphosphonic acid, arylphosphonic acid, such as phenylphosphonic acid and benzylphosphonic acid, and phosphonic acid bearing a polymerizable substituent. Suitable examples of a phosphoric acid and/or a derivative thereof include phosphoric acid wherein a part (in particular only a part, but not all) of the hydroxy groups are esterified, for instance phosphoric acid 2-hydroxyethyl methacrylate ester, commercially available as "Miramer A99", as represented by the following structural formula:

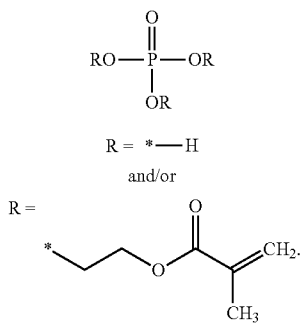

In an embodiment, the at least one stabilizer comprises at least one complexing agent (chelating agent). The term "complexing agent" or "chelating agent", as used herein, may in particular denote a compound which may act as a ligand in a complex, thereby shielding or blocking another compound (i.e. the complexed compound). In particular, the complexing agent may include at least one aromatic azo compound, more specifically at least one aromatic azo compound having a hydroxy group in ortho-position with regard to an azo group. Suitable examples thereof include Sudan 2, Sudan orange, 4-phenylazophenol, 2,2-dihydroxyazobenzene, Tropaepolin O and thiazolylazo resorcinol. Further suitable complexing agents include ammonium oxalate (AO) and/or ethylenebis(diphenylphosphine) (EBP).

In an embodiment, the at least one stabilizer comprises at least one radical scavenger, in particular at least one phenolic radical scavenger, and at least one phosphorous containing compound, in particular at least one phosphonic acid and/or at least one phosphoric acid and/or a derivative thereof.

In an embodiment, the at least one stabilizer comprises at least one radical scavenger, in particular at least one phenolic radical scavenger, and at least one complexing agent, in particular at least one aromatic azo compound.

In an embodiment, the at least one stabilizer comprises at least one radical scavenger, in particular at least one phenolic radical scavenger, at least one phosphorous containing compound, in particular at least one phosphonic acid and/or at least one phosphoric acid and/or a derivative thereof, and at least one complexing agent, in particular at least one aromatic azo compound.

The content of the at least one stabilizer (or the total content of stabilizers) may be in particular from 0.001 to 10 wt.-%, such as from 0.01 to 7.5 wt.-%, in particular from 0.1 to 6 wt.-%, in particular from 0.5 to 5 wt.-%, in particular from 2 to 4 wt.-%, with respect to the total weight of the resin composition. For instance, an at least one radical scavenger and/or an at least one phosphorous containing compound may be comprised in an amount of from 0.1 to 10 wt.-%, such as from 0.2 to 7.5 wt.-%, in particular from 0.5 to 6 wt.-%, in particular from 1 to 5 wt.-%, in particular from 2 to 4 wt.-%, with respect to the total weight of the resin composition, whereas an at least one complexing agent may be comprised in an amount of from 0.001 to 5 wt.-%, such as from 0.01 to 2.5 wt.-%, in particular from 0.1 to 2 wt.-%, in particular from 0.25 to 1.5 wt.-%, in particular from 0.5 to 1 wt.-%, with respect to the total weight of the resin composition.

In an embodiment, the resin composition may further comprise at least one additive selected from the group consisting of a pigment, an inorganic filler, an organic filler, a dispersing agent, a levelling agent, a slip agent, a light absorber, a rheology modifier and a defoaming additive.

By the presence of an additive, such as a pigment, an inorganic filler and/or an organic filler, the products obtained by the thiol-yne-alkene reaction, for instance the products of a printing method utilizing the resin composition, may be provided with additional specific tailor-made advantageous properties, as desired. The presence of a dispersing agent, a levelling agent, a slip agent and/or a light absorber in the resin composition may be in particular helpful to improve the efficiency of the thiol-yne-alkene reaction and/or to increase the homogeneity of the resin composition and of the polymer network formed. Among them, a levelling agent and a slip agent may influence the film formation in a stereolithography process.

The pigment may be an organic or an inorganic pigment. The pigment is not particularly limited and any pigment customarily used for printing for example may be used, as long as it does not substantially impair the thiol-yne-alkene reaction between the yne component, the alkene component and the thiol component in the resin composition. Suitable examples of pigments are disclosed for instance in paragraphs [0128] to [0138] of WO 2008/074548, column 14, line 39 to column 15, line 46 of U.S. Pat. No. 6,045,607, pages 12 to 16 of WO 2005/049744 further providing additional references, the disclosures of all of which are incorporated herein by reference. The pigment may be surface-treated so as to improve its dispersibility in the resin composition.

The inorganic filler is not particularly limited, as long as it does not substantially impair the thiol-yne-alkene reaction between the yne component, the alkene component and the thiol component in the resin composition. In particular, the inorganic filler may be any one of (or a combination) of calcium carbonate, aluminum oxide, zirconium oxide, silicium nitride, a calcium phosphate, such as tricalciumphosphate, and/or a hydroxyapatite, which are in particular suitable if the product obtained after the thiol-yne-alkene reaction, for instance by a printing method, is used as an implant, a bone substitute and/or a dental product, such as a dental prosthesis. Further appropriate examples of inorganic fillers are disclosed on pages 24 to 27 of WO 2013/052328 A1, the disclosure of which is incorporated herein by reference.

The organic filler is not particularly limited, as long as it does not substantially impair the thiol-yne-alkene reaction between the yne component, the alkene component and the thiol component in the resin composition. In particular, the organic filler may be a heparin, a collagen and/or a gelatine, which are in particular suitable if the product obtained after the thiol-yne-alkene reaction, for instance by a printing method, is used as an implant, a bone substitute and/or a dental product, such as a dental prosthesis. In addition, the organic filler may comprise physiologically active compounds, such as proteins, enzymes, peptides, antibodies, drugs, and the like. Further appropriate examples of organic fillers are disclosed on pages 24 to 27 of WO 2013/052328 A1 and the paragraph bridging pages 7 and 8 of WO 2012/103445 A2, the disclosures of which are incorporated herein by reference.

The dispersing agent is not particularly limited, as long as it does not substantially impair the thiol-yne-alkene reaction between the yne component, the alkene component and the thiol component in the resin composition. Suitable examples of the dispersing agent include Disper Byk 102; Disper Byk 106; Disper Byk 110; Disper Byk 162; Disper Byk 182; Disper Byk 2000; Disper Byk 2008; Disper Byk 2025; Disper Byk 2164; and Disper Byk 2205.

The levelling agent is not particularly limited, as long as it does not substantially impair the thiol-yne-alkene reaction between the yne component, the alkene component and the thiol component in the resin composition. Suitable examples of the levelling agent include Byk-302; Byk-350; Byk-399; Byk-381; and Byk-3550.

The slip agent is not particularly limited, as long as it does not substantially impair the thiol-yne-alkene reaction between the yne component, the alkene component and the thiol component in the resin composition. Suitable examples of the slip agent include Byk-307; Byk-377; Ceraflour 991; and Ceraflour 925.

The light absorber is not particularly limited, as long as it does not substantially impair the thiol-yne-alkene reaction between the yne component, the alkene component and the thiol component in the resin composition. In particular, the light absorber may be an ultraviolet and/or visible light absorber. Suitable examples of the light absorber include ethylhexylmethoxycinnamat; butylmethoxydibenzoylmethan; benzylidencampher sulfonic acid; octyltriazon; phenylbenzimidazol sulfonic acid; octocrylen; 2-hydroxy-4-methoxybenzophenon; 2-hydroxy-4-methoxybenzophenon-5-sulfonic acid; 3-benzyliden-boman-2-on; 4-tert.-butyl-4'-methoxy-dibenzoyl-methan; 2-[-4-(diethylamino)-2-hydroxybenzoyl] benzoesäurehexylester3; dioctylbutamidotriazon; 2-ethylhexyl-2-hydroxybenzoat; and 4-methylbenzylidencampher.

The rheology modifier is not particularly limited, as long as it does not substantially impair the thiol-yne-alkene reaction between the yne component, the alkene component and the thiol component in the resin composition. Suitable examples of the rheology modifier include Tixogel-EZ 100; Viscobyk-4010; Rheocin; and Rheotix-240.

The defoaming additive is not particularly limited, as long as it does not substantially impair the thiol-yne-alkene reaction between the yne component, the alkene component and the thiol component in the resin composition. Suitable examples of the defoaming additive include Byk-088; Byk-1790; Byk-1794; and Byk-1794.

The content of the at least one additive selected from the group consisting of a pigment, an inorganic filler, an organic filler, a dispersing agent, a levelling agent, a slip agent, a light absorber, a rheology modifier and a defoaming additive, in particular its total content, may be from 0.1 to 70 wt.-%, such as from 0.2 to 60 wt.-%, in particular from 0.5 to 50 wt.-%, in particular from 1 to 40 wt.-%, in particular from 2 to 30 wt.-%, with respect to the total weight of the resin composition.

Further components or ingredients may be contained in the resin composition.

For example, further monomers other than the above described yne, thiol and alkene monomers may be contained in the resin composition, which may in particular copolymerize with the yne, thiol and/or alkene monomers and which may thereby impart further specific characteristics to the (co-)polymer obtained by polymerizing some or all components of the resin composition.

Moreover, dispersants and/or wetting agents may be contained in the resin composition.

In particular, the resin composition may further contain surfactants suitable as dispersants and/or wetting agents, such as anionic surfactants, cationic surfactants, nonionic surfactants and/or ampholytic surfactants.

Suitable examples of anionic surfactants include surfactants comprising carboxylate, sulfate, phosphate and/or sulfonate groups, for instance amino acid derivatives, fatty alcohol ether sulfates, fatty alcohol sulfates, soaps (such as sodium soaps and/or potassium soaps) alkylphenol ethoxylates, fatty alcohol ethoxylates, alkyl sulfates, olefin sulfates and/or alkyl phosphates.

Suitable examples of cationic surfactants include quaternary ammonium or quaternary phosphonium compounds, for instance tetraalkyl ammonium salts, N,N-dialkyl imidazoline compounds, dimethyl distearyl ammonium compounds, N-alkyl pyridine compounds and/or ammonium chlorides.

Suitable examples of nonionic surfactants include ethoxylates, for instance ethoxylated addition products of alcohols, such as polyoxyalkylene polyols, amines, fatty acids, alkyl phenols, ethanol amides, polysiloxanes and/or fatty acid esters, alkyl or alkylphenyl polyglycol ether, such as fatty alcohol polyglycol ether or fatty acid amides, alkyl glycosides, sugar esters, sorbitan esters, polysorbates and/or trialkyl amine oxides; ester and/or amides pf poly(meth)acrylic acids with polyalkylene glycols and/or amino polyalkylene glycols, all of which may be terminated by alkyl groups on one side.

Suitable examples of ampholytic surfactants include amphoteric electrolytes, also called ampholytes, such as amino carboxylic acids and/or betaines.

Further appropriate examples of additional components or ingredients, in particular of dispersants and surfactants, are disclosed on pages 34 to 37 of WO 2013/087427 A1, the disclosure of which is incorporated herein by reference.

The resin composition may be solid, semi-solid (pasty) or liquid. Since the yne monomer, the thiol monomer and/or the alkene monomer are typically liquid, the resin composition may be in particular a solution, an emulsion or a dispersion (in particular a solid-liquid dispersion, such as a suspension).

The resin composition may be in particular substantially solvent-free, such as substantially water-free. The term "substantially solvent-free", as used herein, may in particular denote that the resin composition comprises not more than 15 wt.-% of a solvent, in particular not more than 10 wt.-%, in particular not more than 5 wt.-%, in particular not more than 2 wt.-%, in particular not more than 1 wt.-%.

Accordingly, the resin composition may in particular contain substantially no solvent, such as a polar solvent or an apolar solvent, for instance water, an alcoholic solvent (such as methanol, ethanol, glycol, 1-propanol, 2-propanol (IPA), propylene glycol, 1-butanol, 2-butanol, isobutyl alcohol, butylene glycol, and the like), an ether solvent (such as dimethyl ether, diethyl ether, tert-butyl methyl ether, 1,4-dioxane, tetrahydrofuran (THF), and the like), an ester solvent (such as ethyl acetate, and the like), a carbonate solvent (such as dimethyl carbonate, diethyl carbonate, and the like), a halogenated alkane solvent (such as dichloromethane, trichloromethane, tetrachloromethane, 1,2-dichloroethane, and the like), a nitrile solvent (such as acetonitrile, and the like), an aldehyde or ketone solvent (such as acetone, and the like), an amide solvent (such as dimethylformamide (DMF), and the like), a sulfoxide solvent (such as dimethylsulfoxide (DMSO), and the like), an acid solvent (such as formic acid, acetic acid, and the like), a hydrocarbon solvent (such as pentane, cyclopentane, hexane, cyclohexane, heptane, octane, and the like), or an aromatic solvent (such as benzene, toluene, and the like).

In an embodiment, the resin composition may comprise a small amount of a solvent, such as any one of the solvents listed above. For instance the resin composition may comprise up to 15 wt.-% of a solvent, in particular up to 10 wt.-%. Hereby, the viscosity of the resin composition may be appropriately adjusted, in particular lowered in case the viscosity would otherwise be very high, which might be advantageous with regard to the printability of the resin composition.

In an embodiment, the resin composition is substantially solvent-free, in particular substantially water-free, and the at least one compound C3 having at least one carbon-carbon double bond of the resin composition has at least one functional group selected from the group consisting of an allyl functional group, an acrylate functional group and a methacrylate functional group. Hereby, a particular advantageous resin composition may be obtained.

In an embodiment, the at least one compound C1 and the at least one compound C3 may form one (single) compound. In other words, the resin composition may comprise at least one compound C4 having at least one terminal alkyne functional group and at least one carbon-carbon double bond. In an embodiment, the at least one compound C4 may be comprised in addition to the at least one compound C1 and/or the at least one compound C3, for example the resin composition may comprise at least on compound C4, at least one compound C2 and at least one compound C3. In another embodiment, the at least one compound C4 may be comprised instead of the at least one compound C1 and the at least one compound C3, for example the resin composition may comprise at least on compound C4 and at least one compound C2. The at least one terminal alkyne functional group and the at least one carbon-carbon double bond of the compound C4 may in particular be those, as illustrated in the foregoing. In addition, the resin composition comprising at least one compound C4 may further comprise further ingredients or components, as described in detail above. By comprising at least one compound C4, the resin composition may show particularly advantageous properties, such as a high reaction (polymerization) speed (high curing velocity), a particularly low content of residual monomers, a particularly low shrinkage of the resulting polymer, excellent mechanical properties (such as elastic modulus) of the resulting polymer, and the like. For example, the at least one compound C4 may have at least one terminal alkyne functional group and at least one allyl functional group.

In a second aspect, an exemplary embodiment of the invention relates to the use of the resin composition as described herein as or in an ink, which may be for instance suitable in a printing method, as described in further detail below. In particular, the resin composition may be used as an ink (a printing ink), i.e. the resin composition itself may be directly used as an ink. Alternatively, the resin composition may be used in an ink (a printing ink), i.e. as a component or an ingredient of an ink together with appropriate one or more further components or ingredients, typically used in an ink.

In a third aspect, an exemplary embodiment of the invention relates to a kit comprising:
  at least one compound C1 having at least one terminal alkyne functional group;
  at least one compound C2 having at least two thiol functional groups;
  at least one compound C3 having at least one carbon-carbon double bond;
  at least one photoinitiator; and
  optionally at least one stabilizer.

The at least one compound C1, the at least one compound C2, the at least one compound C3, the at least one photoinitiator as well as the optional at least one stabilizer may in particular be those as defined in detail above with regard to the resin composition according to embodiments of the invention.

The components may be in particular provided in a spatially separated manner in the kit, in particular the kit-of-parts. In particular, the components C1 and C3 on the one hand and the component C2 on the other hand may be provided in separate compartments of the kit. This might be advantageous if the components C1 and/or C3 and/or the at least one component C2 are reactive to such an extent that it/they tends/tend to (prematurely) react with the other component/with each other, even when stored in the dark (such as when packaged by means of a light nontransparent material) and/or at low temperature (such as at a temperature of not more than 10° C., in particular not more than 5° C., such as not more than 0° C.). In addition, when the compound C1 having at least one terminal alkyne functional group and the compound C3 having at least one carbon-carbon double bond on the one hand and the compound C2 having at least two thiol functional groups on the other hand are provided in separate compositions (for instance spatially separated manner in a kit-of-parts), which are combined not until immediately prior to printing, a stabilizer may be dispensable (but may be nevertheless contained, for instance in smaller amounts).

Further ingredients or components, as described in detail above with regard to the resin composition, in particular the photoacid, the photobase, the at least one additive selected from the group consisting of a pigment, an inorganic filler, an organic filler, a dispersing agent, a levelling agent, a slip agent, a light absorber, a rheology modifier and a defoaming additive, the further monomers other than the yne, thiol and alkene monomers, surfactants, dispersants, wetting agents and/or sequestering agents, may be contained independently from each other in any one of the compartment of compounds C1 and C3 and/or the compartment of compound C2 as well as in any additional compartment of the kit.

In particular, the kit may be a two-, three-, four-, five- or multi-component system, such as a 2K system, a 3K system, a 4K system, a 5K system and the like.

Prior to use, for instance in a printing method, the components contained in separate compartments of the kit are mixed. The mixing may be carried out manually or (semi-)automatically by an appropriate device or dispenser. The components contained in separate compartments of the kit may be in particular mixed not more than 48 hours, not more than 24 hours, not more than 12 hours, not more than 6 hours, not more than 4 hours, not more than 3 hours, not more than 2 hours, not more than 90 minutes, not more than 60 minutes, not more than 45 minutes, not more than 30 minutes, not more than 25 minutes, not more than 20 minutes, not more than 15 minutes, not more than 10 minutes, not more than 7.5 minutes, not more than 5 minutes, not more than 4 minutes, not more than 3 minutes, not more than 2 minutes, not more than 90 seconds, not more than 60 seconds, not more than 45 seconds, not more than 30 seconds, not more than 25 seconds, not more than 20 seconds, not more than seconds, not more than 10 seconds, not more than 7.5 seconds, not more than 5 seconds, not more than 4 seconds, not more than 3 seconds, not more than 2 seconds, not more than 1 second, prior to use, for instance in a printing method.

In a fourth aspect, an exemplary embodiment of the invention relates to the use of the kit as described herein for preparing a resin composition, in particular the resin composition as described herein, suitable for use as or in an ink, which may be for instance suitable in a printing method, as described in further detail below.

For preparing the resin composition, the components contained in separate compartments of the kit may be mixed. The mixing may be carried out manually or (semi-)automatically by an appropriate device or dispenser.

In a fifth aspect, an exemplary embodiment of the invention relates to a printing method comprising the steps of
  providing (for instance printing) a first ink portion comprising at least one compound C1 having at least one terminal alkyne functional group and at least one compound C3 having at least one carbon-carbon double bond;
  providing (for instance printing) a second ink portion comprising at least one compound C2 having at least two thiol functional groups;
  wherein at least one of the first and the second ink portions further comprises at least one photoinitiator;
  forming a resin composition from the first and the second ink portions (for instance by mixing the first and the second ink portions), immediately followed by irradiating at least a part of the resin composition with an energy-carrying activation beam so as to cause polymerization of the at least a part of the resin composition and so as to obtain a polymer.

The at least one compound C1, the at least one compound C2, the at least one compound C3 and the at least one photoinitiator may in particular be those as defined in detail above with regard to the resin composition according to embodiments of the invention.

The term "immediately" as used herein may in particular denote a time period during which no significant polymerization reaction, in particular thiol-yne-alkene reaction, occurs, which time period may largely vary depend on the reactivities of the individual components, as it will be apparent to a person skilled in the art. Thus, the term "immediately" may for instance mean not more than 48 hours, not more than 24 hours, not more than 12 hours, not more than 6 hours, not more than 4 hours, not more than 3 hours, not more than 2 hours, not more than 90 minutes, not more than 60 minutes, not more than 45 minutes, not more than 30 minutes, not more than 25 minutes, not more than 20 minutes, not more than 15 minutes, not more than 10 minutes, not more than 7.5 minutes, not more than 5 minutes, not more than 4 minutes, not more than 3 minutes, not more than 2 minutes, not more than 90 seconds, not more than 60 seconds, not more than 45 seconds, not more than 30 seconds, not more than seconds, not more than 20 seconds, not more than 15 seconds, not more than 10 seconds, not more than 7.5 seconds, not more than 5 seconds, not more than 4 seconds, not more than 3 seconds, not more than 2 seconds, not more than 1 second.

In an embodiment, at least one of the first and the second ink portion may further comprise at least one stabilizer, in particular at least one stabilizer or combination of stabilizers (in which case one or more types of stabilizers may be contained in the first ink portion and one or more (other) types of stabilizers may be contained in the second ink portion) as defined in detail above with regard to the resin composition according to embodiments of the invention. While a stabilizer may be dispensable when the compound C1 having at least one terminal alkyne functional group and the compound C3 having at least one carbon-carbon double bond on the one hand and the compound C2 having at least two thiol functional groups on the other hand are provided in separate ink portions, which are combined not until immediately prior to printing, the use of a stabilizer might nevertheless be advantageous for adequately controlling or adjusting the polymerization reaction, in particular the thiol-yne-alkene reaction. For this, it might be sufficient that the at least one stabilizer is contained in smaller amounts as it may be contained in a resin composition configured to be stored for a long time.

In an embodiment, the method further comprises the step of heating the first ink portion and/or the second ink portion, in particular before (prior to) and/or upon (during) providing (for instance printing) the first ink portion and/or the second ink portion. This might be advantageous for instance if the viscosity of the first ink portion and/or the second ink portion is high, so that the viscosity of the first ink portion and/or the second ink portion may be lowered by heating, which may facilitate the printing process. A high viscosity of the first ink portion and/or the second ink portion may for instance occur in cases where the at least one compound C1 has at least two terminal alkyne functional groups, where the monomers exhibit various interactions (such as hydrogen bonds) with each other or where the first ink portion and/or the second ink portion comprises a large amount of filler or any other viscosity increasing compound.

In an embodiment, the first ink portion and/or the second ink portion may be heated to a temperature within the range of from 40° C. to 120° C., for instance 50° C. to 100° C.

In a sixth aspect, an exemplary embodiment of the invention relates to a printing method comprising the steps of
  providing (for instance printing) a resin composition as described herein; and
  irradiating at least a part of the resin composition with an energy-carrying activation beam so as to cause polymerization of the at least a part of the resin composition and so as to obtain a polymer.

In an embodiment, the method further comprises the step of heating the resin composition, in particular before (prior to) and/or upon (during) providing (for instance printing) the resin composition. This might be advantageous for instance if the viscosity of the resin composition is high, so that the viscosity of the resin composition may be lowered by heating, which may facilitate the printing process. A high viscosity of the resin composition may for instance occur in cases where the at least one compound C1 has at least two terminal alkyne functional groups, where the monomers exhibit various interactions (such as hydrogen bonds) with each other or where the resin composition comprises a large amount of filler or any other viscosity increasing compound.

In an embodiment, the resin composition may be heated to a temperature within the range of from 40° C. to 120° C., for instance 50° C. to 100° C.

In an embodiment, the printing method may be a three-dimensional printing method.

The term "three-dimensional printing method", as used herein, in particular denotes that the product of the printing method extends in three directions (for example, length, width and height). Thus, the product of a three-dimensional printing method may be in particular a three-dimensional object.

The three-dimensional printing method may be in particular any one selected from the group consisting of stereolithography (SLA), two-photon absorption (TPA) polymerization, digital light processing (DLP), reactive laser sintering (RLS), solid ground curing (SGC), multi jet modeling (MJM) or a combination thereof. In view of its high resolution, stereolithography (SLA) may be preferred.

In the step of irradiating at least a part of the resin composition with an energy-carrying activation beam (which may also be referred to as an irradiation step or a curing step), a thiol-yne-alkene reaction may be caused at the irradiated part of the resin composition with the result that the yne component, the thiol component and the alkene component undergo a cross-linking (polymerization) reaction at the irradiated part and consequently a polymer is formed at the irradiated part of the resin composition.

In particular, the irradiation may be carried out in a controlled manner, in particular controlled by a computer system, so as to form a desired pattern or structure of the resulting polymer.

The term "at least a part of the resin composition" may in particular mean that not 100% of the resin composition is exposed to the energy source. In particular, the term "at least a part of the resin composition" may mean that at least 5%, in particular at least 10%, in particular at least 15%, in particular at least 20%, in particular at least 25%, in particular at least 30%, in particular at least 35%, in particular at least 40%, in particular at least 45%, in particular at least 50%, in particular at least 55%, in particular at least 60%, in particular at least 65%, in particular at least 70%, in particular at least 75%, in particular at least 80% of the resin composition is exposed to the energy source and it may mean that in particular not more than 95%, in particular not more than 90%, in particular not more than 85%, in particular not more than 80%, in particular not more than 75%, in particular not more than 70%, in particular not more than 65%, in particular not more than 60%, in particular not more than 55%, in particular not more than 50%, in particular not more than 45%, in particular not more than 40%, in particular not more than 35%, in particular not more than 30%, in particular not more than 25%, in particular not more than 20% of the resin composition is exposed to the energy source.

It might be advantageous to carry out the irradiation step under an inert gas atmosphere (such as under a $N_2$, $CO_2$, or a noble gas, in particular Ar, atmosphere), while it is also possible to carry out this step under ambient gas atmosphere, such as air, or even under (substantially) pure oxygen.

The duration of the irradiation step is not particularly limited, and may be appropriately selected by a person skilled in the art, depending in particular on the type of the printing method and the components of the resin composition (in particular their reactivity). For instance, suitable times (durations) for irradiation may be from 1 ms to 1 h, in particular from 1 s to 1 min.

The intensity of irradiation is not particularly limited, and may be appropriately selected by a person skilled in the art, depending in particular on the type of the printing method, the components of the resin composition and the duration of the step. For instance, the intensity may be from 0.0001 to 20 $W/cm^2$, in particular from 0.01 to 5 $W/cm^2$.

In an embodiment, the method may further comprise a step of post-curing the polymer during and/or after irradiating the at least part of the resin composition. Thus, the irradiation step may comprise or may be followed by a step of post-curing, wherein the initially formed polymer is further or again provided with actinic energy. For instance, in case of stereolithography, the (initially) formed polymer may be further or again irradiated with ultraviolet radiation in a post-curing step. The post-curing may in particular carried out at an elevated temperature, for instance in a range of from 30 to 80° C.

In an embodiment, the energy-carrying activation beam may in particular comprise electromagnetic radiation (in particular actinic radiation).

In particular, the energy-carrying activation beam may be at least one selected from the group consisting of ultraviolet radiation (such as having a wavelength of from 10 to 380 nm, in particular from 200 to 380 nm, in particular from 250 to 380 nm) and visible light radiation (such as having a wavelength of from 380 to 780 nm).

In an embodiment, the printing method may be a solvent-free printing method. In particular, those solvents as described in detail above with regard to the resin composition according to embodiments of the invention are preferably not used in the printing method.

In an embodiment, the method may further comprise a step of cleaning the polymer, in particular of removing unreacted residual monomers (such as at least one compound C1, compound C2 and compound C3) from the polymer.

In an embodiment, the step of cleaning comprises contacting the polymer with a cleaning composition comprising an alkaline compound, a surfactant and an appropriate solvent. By taking this measure, residual monomers may be precipitated due to an alkaline catalyzed thiol-ene reaction and/or thiol-yne reaction and the thus formed precipitates may be removed by the cleaning composition (e.g. a cleaning solution).

Further details about the (optional) cleaning step, in particular about the cleaning composition, will be explained in further detail below with regard to the eleventh aspect of embodiments of the invention, the disclosure of which may also be combined with the printing methods of the fifth and sixth aspect.

In a seventh aspect, an exemplary embodiment of the invention relates to a polymer obtainable by the printing method as described herein. The polymer may not only be defined by the components of the resin composition, but also it may be defined by the specific pattern and/or (three-dimensional) structure that it has obtained by the printing method. The chemical structure of the polymer may in particular depend on the components of the resin composition, but also on the specific conditions of the printing method that may influence the degree of crosslinking within the polymer, whereas the geometrical structure of the polymer may in particular depend on the specific conditions of the printing method, such as the specific pattern and/or (three-dimensional) structure imparted to the polymer by the printing method, but also on the components of the resin composition.

In an eighth aspect, an exemplary embodiment of the invention relates to an article comprising or formed from the polymer as described herein. The article may consist of the polymer with or without any further modifications, such as re-shaping, or the article may comprise the polymer in addition to further components or ingredients, as desired according to specific purposes. For instance, the article may comprise the polymer and a coating, such as a nanocoating. The article may also be formed from the polymer.

In an embodiment, the article may be a medical device or a biomedical device. The medical and/or biomedical device may be in particular selected from the group consisting of an implant, a bone substitute, a tissue substitute and a dental product.

Since a medical and/or biomedical device is typically exposed to a human or animal body upon use, the article should preferably be biocompatible. In particular, the article should not substantially disturb/impart the physiological functions or properties of that part of a human or animal body to be in contact with the article. In addition, the article should not release any harmful compounds or any otherwise detrimental compounds to that part of a human or animal body to be in contact with the article. Since the polymer and consequently also the article is obtained as a result of a thiol-yne-alkene reaction, the polymer has a very low residual monomer content, a high chemical stability and a low shrinkage so that the polymer as well as the article is not only highly biocompatible, but is also in particular suitable as a medical and/or biomedical device.

In an embodiment, the article (as well as the polymer) may be substantially biodegradable. This may accomplished for instance if at least one of the compounds C1, C2 and C3 (for instance, at least C1, at least C2, at least C3, at least C1 and C2, at least C1 and C3, at least C2 and C3, or any one of C1, C2 and C3) comprises a carbamate functional group, a carbonate functional group and/or an ester functional group, or any other hydrolysable functional group, in particular an ester functional group. Additionally or alternatively, a substantial biodegradability of the article (as well as of the polymer) may be achieved for instance by using a relatively large amount of thiol groups-containing compounds C2 compared to the other two compounds C1 and C3.

In an alternative embodiment, the article (as well as the polymer) may be substantially non-biodegradable.

The term "substantially" as used herein in particular denotes at least 50%, in particular at least 60%, in particular at least 70%, in particular at least 75%, in particular at least 80%, in particular at least 85%, in particular at least 90%, in particular at least 92.5%, in particular at least 95%, in particular at least 96%, in particular at least 97%, in particular at least 98%, in particular at least 99%, in particular up to 100%, unless specifically stated otherwise.

It might also be advantageous that the product (such as the polymer and/or the article) is at least partially biodegradable and at least partially non-biodegradable, for instance if a certain persistent mechanical support is desired, or that a part of the product biodegrades relatively fast whereas a part of the product biodegrades relatively slowly, which might be in particular advantageous when using the product as an implant, a bone substitute and/or a tissue substitute. Such products may in particular be derived from a resin composition comprising combinations of ether, carbamate and/or carbonate functional groups, in particular combinations of ether and carbamate functional groups, combinations of ether and carbonate functional groups, combinations of carbamate and carbonate functional groups, and combinations of ether, carbamate and carbonate functional groups.

In an embodiment, at least a part of a surface of the article is modified by a coating, in particular by a nanocoating or monomolecular coating.

The term "at least a part of a surface of the article" may in particular mean at least 5%, in particular at least 10%, in particular at least 15%, in particular at least 20%, in particular at least 25%, in particular at least 30%, in particular at least 35%, in particular at least 40%, in particular at least 45%, in particular at least 50%, in particular at least 55%, in particular at least 60%, in particular at least 65%, in particular at least 70%, in particular at least 75%, in particular at least 80%, in particular at least 85%, in particular at least 90%, in particular at least 95%, in particular 100% of a surface of the article is coated or modified by a coating.

In an embodiment, the coating may be an antimicrobial coating. Hereby, the article may be provided with antimicrobial properties, which may in particular be advantageous when the article is configured as a medical and/or biomedical device. A suitable example of a material for an antimicrobial coating includes a quaternary amine, which may for instance efficiently be bonded (attached) to (remaining) thiol functional groups on a surface of the article by means of a thiol-Michael reaction. As discussed above, the ratio of the monomers in the resin composition may be adjusted such that some thiol functional groups may remain in the polymer formed after completion of the thiol-yne-alkene reaction, in particular on the surface of the polymer or of an article comprising or formed from the polymer, which residual thiol functional groups may serve as a binding site capable for coupling the polymer or the article with a coating material, such as a quaternary amine. Thereby, a surface-modified or coated, in particular antimicrobially coated, polymer or article may be obtained.

In an embodiment, the article is a shape memory article, i.e. exhibits a shape memory behavior. In particular, the article may comprise or consist of a shape memory polymer obtainable from the resin composition as described herein.

The term "shape memory" as used herein denotes the ability of the polymer or the article to return from a deformed state (temporary shape) at least partly to its original (permanent) shape induced by an external stimulus (trigger), such as a temperature change.

In a ninth aspect, an exemplary embodiment of the invention relates to the use of the polymer or of the article according to embodiments of the invention in a medical or biomedical application.

In particular, the medical application comprises any one selected from the group consisting of an implantation, a bone substitution or replacement, a tissue substitution or replacement, and a dental application.

In a tenth aspect, an exemplary embodiment of the invention relates to a composition comprising:
 at least one compound C1 having at least one terminal alkyne functional group and/or at least one compound C3 having at least one carbon-carbon double bond;
 at least one compound C2 having at least two thiol functional groups; and
 at least one stabilizer selected from the group consisting of a radical scavenger, a phosphorous containing compound and a complexing agent.

The at least one compound C1, the at least one compound C2, the at least one compound C3, as well as the at least one stabilizer, in particular the radical scavenger, the phosphorous containing compound and the complexing agent, may be those as defined in detail above with regard to the resin composition according to embodiments of the invention.

In an embodiment, the composition comprises at least two compounds C3 having at least one carbon-carbon double bond, in particular a compound C3a having at least one (meth)acrylate functional group (i.e. an acrylate and/or a methacrylate functional group) and a compound C3b having at least one allyl functional group, such as an allyl ether. Thus, the composition may comprise at least one compound C3a having at least one (meth)acrylate functional group, at least one compound C3b having at least one allyl functional group (in particular an allyl ether), at least one compound C2 having at least two thiol functional groups, and at least one stabilizer selected from the group consisting of a radical scavenger, a phosphorous containing compound and a complexing agent.

The inventors have found that specific stabilizers, i.e. a radical scavenger, a phosphorous containing compound and/or a complexing agent, are also capable of stabilizing (in particular improving the storage stability of) a composition comprising a thiol monomer and at least one of an yne monomer and an alkene monomer. The at least one stabilizer (or combination of several stabilizers) may in particular avoid or at least reduce a premature reaction (in particular a premature initiation and/or propagation) of a compound C1 having at least one terminal alkyne functional group and/or a compound C3 having at least one carbon-carbon double bond with a compound C2 having at least two thiol functional groups.

In an embodiment, the at least one stabilizer comprises at least one radical scavenger. The term "radical scavenger", as used herein, may in particular denote a compound which may undergo a reaction with a radical (such as a compound having an unshared electron pair), thereby eliminating or trapping the radical. In particular, the radical scavenger may include a phenolic radical scavenger or a phenolic antioxidant. Suitable examples of the radical scavenger include a hydroquinone, such as hydroquinone monomethyl ether (HQME), t-butyl catechol, pyrogallol or an ether thereof, anthralin, oxyhydrochinon, propyl gallat, lauryl gallat, butylhydroxytoluene (BHT, 2,6-di-tert-butyl-4-methylphenol), butylated hydroxyanisole (BHA, 2-tert-butyl-4-hydroxyanisole and/or 3-tert-butyl-4-hydroxyanisole) and/or di- or trihydroxybenzaldehydes, in particular 2,4-dihydroxybenzaldehyde (2,4-DHB), 3,4-dihydroxybenzaldehyde (3,4-DHB), 3,5-dihydroxybenzaldehyde (3,5-DHB), 2,5-dihydroxybenzaldehyde (2,5-DHB), 2,3-dihydroxybenzaldehyde (2,3-DHB) and/or 2,3,4-trihydroxybenzaldehyde (2,3,4-THB). Particular suitable examples of the radical scavenger include pyrogallol, anthralin, oxyhydrochinon, propyl gallat, BHT and the di- or trihydroxybenzaldehydes exemplified above.

In an embodiment, the at least one stabilizer comprises at least one phosphorous containing compound, in particular at least one phosphonic acid and/or at least one phosphoric acid and/or a derivative (in particular an ester) thereof. Such stabilizer compounds may in particular suitable for suppressing a (premature) thiol-Michael reaction. Suitable examples of a phosphonic acid include alkylphosphonic acid, vinylphosphonic acid, arylphosphonic acid, such as phenylphosphonic acid and benzylphosphonic acid, and phosphonic acid bearing a polymerizable substituent. Suitable examples of a phosphoric acid and/or a derivative thereof include phosphoric acid wherein a part (in particular only a part, but not all) of the hydroxy groups are esterified, for instance phosphoric acid 2-hydroxyethyl methacrylate ester, commercially available as "Miramer A99", as represented by the following structural formula:

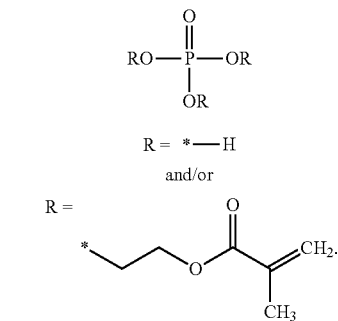

In an embodiment, the at least one stabilizer comprises at least one complexing agent (chelating agent). The term "complexing agent" or "chelating agent", as used herein, may in particular denote a compound which may act as a ligand in a complex, thereby shielding or blocking another compound (i.e. the complexed compound). In particular, the complexing agent may include at least one aromatic azo compound, more specifically at least one aromatic azo compound having a hydroxy group in ortho-position with regard to an azo group. Suitable examples thereof include Sudan 2, Sudan orange, 4-phenylazophenol, 2,2-dihydroxyazobenzene, Tropaeolin O and thiazolylazo resorcinol. Further suitable complexing agents include ammonium oxalate (AO) and/or ethylenebis(diphenylphosphine) (EBP).

In an embodiment, the at least one stabilizer comprises at least one radical scavenger, in particular at least one phenolic radical scavenger, and at least one phosphorous containing compound, in particular at least one phosphonic acid and/or at least one phosphoric acid and/or a derivative thereof.

In an embodiment, the at least one stabilizer comprises at least one radical scavenger, in particular at least one phenolic radical scavenger, and at least one complexing agent, in particular at least one aromatic azo compound.

In an embodiment, the at least one stabilizer comprises at least one radical scavenger, in particular at least one phenolic radical scavenger, at least one phosphorous containing compound, in particular at least one phosphonic acid and/or at least one phosphoric acid and/or a derivative thereof, and at least one complexing agent, in particular at least one aromatic azo compound.

The content of the at least one stabilizer (or the total content of stabilizers) may be in particular from 0.001 to 10 wt.-%, such as from 0.01 to 7.5 wt.-%, in particular from 0.1 to 6 wt.-%, in particular from 0.5 to 5 wt.-%, in particular from 2 to 4 wt.-%, with respect to the total weight of the resin composition. For instance, the at least one radical scavenger and/or the at least one phosphorous containing compound may be comprised in an amount of from 0.1 to 10 wt.-%, such as from 0.2 to 7.5 wt.-%, in particular from 0.5 to 6 wt.-%, in particular from 1 to 5 wt.-%, in particular from 2 to 4 wt.-%, with respect to the total weight of the resin composition, whereas the at least one complexing agent may be comprised in an amount of from 0.001 to 5 wt.-%, such as from 0.01 to 2.5 wt.-%, in particular from 0.1 to 2 wt.-%, in particular from 0.25 to 1.5 wt.-%, in particular from 0.5 to 1 wt.-%, with respect to the total weight of the resin composition.

In an eleventh aspect, an exemplary embodiment of the invention relates to a printing method comprising the steps of providing a resin composition comprising at least one compound C1 having at least one terminal alkyne functional group and/or at least one compound C3 having at least one carbon-carbon double bond and at least one compound C2 having at least two thiol functional groups;

irradiating at least a part of the resin composition with an energy-carrying activation beam so as to cause polymerization of the at least a part of the resin composition and so as to obtain a polymer; and contacting the polymer with a cleaning composition comprising an alkaline compound, a surfactant and a solvent.

The at least one compound C1, the at least one compound C2 and the at least one compound C3, may be those as defined in detail above with regard to the resin composition according to embodiments of the invention. In addition, the resin composition may comprise further ingredients or components, as described in detail above with regard to the (resin) composition, in particular at least one photoinitiator, at least one stabilizer, such as a radical scavenger, a phosphorous containing compound and a complexing agent, a photoacid, a photobase, at least one additive selected from the group consisting of a pigment, an inorganic filler, an organic filler, a dispersing agent, a levelling agent, a slip agent, a light absorber, a rheology modifier and a defoaming additive, further monomers other than the yne, thiol and/or alkene monomers, surfactants, dispersants, wetting agents and/or sequestering agents, as exemplified herein.

Moreover, the steps of providing a resin composition and/or of irradiating at least a part of the resin composition with an energy-carrying activation beam as well as the printing technique may be carried out as described in detail above with regard to the printing method of the fifth and sixth aspect. Likewise, additional process steps as exemplified above with regard to the printing method of the fifth and sixth aspect, such as a heating step and/or a post-curing step, may be implemented in the printing method of the eleventh aspect.

The printing method according to the eleventh aspect is in particular characterized by the step of contacting the polymer with a cleaning composition comprising an alkaline compound, a surfactant and a solvent. By taking this measure, residual monomers may be precipitated due to an alkaline catalyzed thiol-ene reaction and/or thiol-yne reaction and the thus formed precipitates may be removed by the cleaning composition (e.g. a cleaning solution). Thus, unreacted residual monomers (such as at least one compound C1, compound C2 and compound C3) may be removed from the polymer and, as a result, the polymer may be cleaned.

Subsequently, precipitates may be removed from the cleaning solution, for instance by filtration, centrifugation and/or decantation of the cleaning solution, so that the cleaning solution may be reused in a further cleaning step. Thus, in an embodiment, the method may further comprises—after the step of contacting the polymer with a cleaning composition—a step of removing solids (such as precipitates) from the cleaning composition. In particular, the step of removing solids from the cleaning composition may include at least one of filtration, centrifugation and/or decantation of the cleaning composition.

The step of contacting the polymer with a cleaning composition may include rinsing or purging the polymer with a cleaning composition and/or immersing or dipping the polymer into a cleaning composition.

In an embodiment, the step of contacting the polymer with a cleaning composition is carried out at a temperature of from 20° C. to 60° C. and/or upon application of ultrasonics. In particular, the step of contacting the polymer with a cleaning composition may be carried out at a (n elevated) temperature of from 20° C. to 60° C., such as from 25° C. to 50° C., in particular from 30° C. to 40° C.

Alternatively or additionally, the step of contacting the polymer with a cleaning composition may be carried upon application of ultrasonics (ultrasound). To this end, for instance an ultrasonic bath, preferably with temperature control or heating equipment, may be used. By taking this/these measures(s), the efficiency of the cleaning step may be increased and the cleaning step may be accomplished within a short period of time.

The cleaning composition may in particular be a cleaning solution, i.e. a clear solution, but may also be a cleaning dispersion or a cleaning suspension, while a (clear) cleaning solution being preferred.

The cleaning composition comprises an alkaline compound, a surfactant (which may also be referred to as "cleaning composition surfactant" hereinafter) and a solvent (which may also be referred to as "cleaning composition solvent" hereinafter). Further ingredients may (but need not) be comprised in the cleaning composition.

The term "alkaline compound", as used herein, may in particular denote a compound having alkaline or basic properties, i.e. which may be capable of increasing the pH value of a composition (such as a solution) containing the alkaline compound. In particular, an alkaline compound may be capable of capturing protons ($H^+$) or hydronium ions ($H_3O^+$) from and/or capable of releasing hydroxide ions ($OH^-$) to a surrounding medium.

In an embodiment, the alkaline compound may comprise inorganic and/or organic compounds. Suitable examples include alkali metal carbonates, alkali metal hydroxides, ammonium hydroxide, ammonia, ammonium derivatives, organic amines, such as ethanolamine, and combinations thereof.

In an embodiment, the cleaning composition surfactant is selected from the group consisting of anionic surfactants, zwitterionic surfactants, amphoteric surfactants, nonionic surfactants, cationic surfactants, such as monovalent cationic surfactants, and combinations thereof.

In an embodiment, the cleaning composition solvent comprises a polar solvent and/or an apolar solvent. Suitable examples include water, an alcoholic solvent (such as methanol, ethanol, glycol, 1-propanol, 2-propanol (IPA), propylene glycol, 1-butanol, 2-butanol, isobutyl alcohol, butylene glycol, and the like), an ether solvent (such as dimethyl ether, diethyl ether, tert-butyl methyl ether, 1,4-dioxane, tetrahydrofuran (THF), and the like), an ester solvent (such as ethyl acetate, and the like), a carbonate solvent (such as dimethyl carbonate, diethyl carbonate, and the like), a halogenated alkane solvent (such as dichloromethane, trichloromethane, tetrachloromethane, 1,2-dichloroethane, and the like), a nitrile solvent (such as acetonitrile, and the like), an aldehyde or ketone solvent (such as acetone, and the like), an amide solvent (such as dimethylformamide (DMF), and the like), a sulfoxide solvent (such as dimethylsulfoxide (DMSO), and the like), an acid solvent (such as formic acid, acetic acid, and the like), a hydrocarbon solvent (such as pentane, cyclopentane, hexane, cyclohexane, heptane, octane, and the like), and/or an aromatic solvent (such as benzene, toluene, and the like).

Embodiments of the invention are further described by the following examples, which are solely for the purpose of illustrating specific embodiments, and are not construed as limiting the scope of the invention in any way.

EXAMPLES

Example 1

The toughness of various 3D printed structures was determined by Charpy impact testing according to the ISO standard 179-1:2010. The used resins comprise thiol monomers (e.g. pentaerythritol tetrakis(3-mercaptopropionate), PETMP), and alkyne monomers (e.g. 1,4-butanediol dibut-1-ynyl ether, Bbut; di(but-3-yn-1-yl) carbonate, DBC), and/or allyl monomers (diallyl (2,2,4-trimethylhexane-1,6-diyl) dicarbamate), and/or methacrylates (e.g. 1,4-butanediol dimethacrylate, BMA; Isobutylmethacrylat, IsobutylMA; 7,7,9-trimethyl-4,13-dioxo-3,14-dioxa-5,12-diazahexadecane-1,16-diyl bis(2-methylacrylate), UDMA), and/or acrylates (1,4-butanediol diacrylate, BA). To the formulations 3 wt % Irgacure TPO-L (IrgTPOL), 0.5 wt % pyrogallol, 2 wt % MiramerA99, 0.05 wt % sudan orange were added. The printed samples were post-cured with 405 nm at 100° C. As reference materials BMA and BA, respectively, and PETMP/alken formulations with 3 wt % IrgTPOL were used. The ratios of the functional groups of the monomers are listed in brackets in table 1.

Table 1 shows the obtained values of the impact strength of the tested mixtures.

TABLE 1

| Components (Ratio func. groups) | Charpy [kJ/m$^2$] |
|---|---|
| PETMP/Bbut/BMA (3:1:3) | 20 +− 8 |
| PETMP/Bbut/BMA (2:1:4) | 17 +− 6 |
| PETMP/Bbut/BMA (2:1:12) | 11 +− 4 |
| PETMP/Bbut/BMA/IsobutylMA (3:1:2.7:0.3) | 18 +− 6 |
| PETMP/Bbut/BMA/IsobutylMA (2:1:3.6:0.4) | 14 +− 4 |
| PETMP/Bbut/BMA/IsobutylMA (2:1:10.8:1.2) | 11 +− 4 |
| PETMP/diallyl (2,2,4-trimethylhexane-1,6-diyl)dicarbamate/BMA (3:2:3) * | 22 +− 8 |
| PETMP/diallyl (2,2,4-trimethylhexane-1,6-diyl)dicarbamate/BMA (2:2:4) * | 14 +− 5 |
| PETMP/DBC/UDMA (3:1:3) | 60 +− 18 |
| PETMP/DBC/UDMA (2:1:4) | 44 +− 14 |
| PETMP/DBC/UDMA (2:1:12) | 28 +− 7 |
| PETMP/diallyl (2,2,4-trimethylhexane-1,6-diyl)dicarbamate/BuBut/BMA (9:2:1:9) | 28 +− 8 |
| PETMP/diallyl (2,2,4-trimethylhexane-1,6-diyl)dicarbamate/BuBut/BMA (6:2:1:12) | 16 +− 7 |
| PETMP/diallyl (2,2,4-trimethylhexane-1,6-diyl)dicarbamate/BuBut/BMA (6:2:1:36) | 10 +− 3 |
| PETMP/diallyl (2,2,4-trimethylhexane-1,6-diyl)dicarbamate/BuBut/BMA/IsobutylMA (9:2:1:8.1:0.9) | 27 +− 8 |
| PETMP/diallyl (2,2,4-trimethylhexane-1,6-diyl)dicarbamate/BuBut/BMA/IsobutylMA (6:2:1:10.8:1.2) | 14 +− 4 |
| PETMP/diallyl (2,2,4-trimethylhexane-1,6-diyl)dicarbamate/BuBut/BMA/IsobutylMA (6:2:1:32.4:3.6) | 10 +− 2 |
| 1,4-butanediol dimethacrylate * | 2 +− 1 |
| PETMP/Bbut/BA (3:1:3) | 15 +− 5 |
| PETMP/Bbut/BA (2:1:4) | 11 +− 2 |
| PETMP/Bbut/BA (2:1:12) | 6 +− 3 |
| PETMP/Bbut/BA/IsobutylMA (3:1:2.7:0.3) | 14 +− 4 |
| PETMP/Bbut/BA/IsobutylMA (2:1:3.6:0.4) | 10 +− 3 |
| PETMP/Bbut/BA/IsobutylMA (2:1:10.8:1.2) | 4 +− 2 |
| PETMP/diallyl (2,2,4-trimethylhexane-1,6-diyl)dicarbamate/BA (3:2:3)* | 11 +− 3 |
| PETMP/diallyl (2,2,4-trimethylhexane-1,6-diyl)dicarbamate/BA (2:2:4)* | 9 +− 2 |
| PETMP/DBC/BA (3:1:3) | 16 +− 5 |
| PETMP/DBC/BA (2:1:4) | 11 +− 4 |
| PETMP/diallyl (2,2,4-trimethylhexane-1,6-diyl)dicarbamate/BuBut/BA (9:2:1:9) | 15 +− 4 |
| PETMP/diallyl (2,2,4-trimethylhexane-1,6-diyl)dicarbamate/BuBut/BA (6:2:1:12) | 11 +− 3 |
| PETMP/diallyl (2,2,4-trimethylhexane-1,6-diyl)dicarbamate/BuBut/BA (6:2:1:36) | 7 +− 2 |
| PETMP/diallyl (2,2,4-trimethylhexane-1,6-diyl)dicarbamate/BuBut/BA/IsobutylMA (9:2:1:8.1:0.9) | 15 +− 4 |
| PETMP/diallyl (2,2,4-trimethylhexane-1,6-diyl)dicarbamate/BuBut/BA/IsobutylMA (6:2:1:10.8:1.2) | 10 +− 3 |
| PETMP/diallyl (2,2,4-trimethylhexane-1,6-diyl)dicarbamate/BuBut/BA/IsobutylMA (6:2:1:32.4:3.6) | 4 +− 2 |
| 1,4-butanediol diacrylate * | 2 +− 1 |

* Comparative examples

The tested resin compositions according to embodiments of the invention have a significantly higher impact strength than the comparative examples. The addition of alkynes and/or alkenes and thiols to (meth)acrylates leads to less shrinkage stress and to a more homogeneous network structure yielding photopolymers with a higher toughness compared to cured resins consisting of (meth)acrylates.

Example 2

The heat deflection temperature (HDT) of various 3D printed structures was determined according to ISO 75-1: 1993 and ISO 75-2:1993 (tested by method B in the flatwise position). The used resins comprise thiol monomers (e.g. pentaerythritol tetrakis(3-mercaptopropionate), PETMP), and/or alkyne monomers (e.g. 1,4-butanediol dibut-1-ynyl ether, BBut; di(but-3-yn-1-yl) carbonate, DBC; di(prop-2-yn-1-yl) carbonate, DPC; di(but-3-yn-1-yl) (2,2,4-trimethylhexane-1,6-diyl)dicarbamate), and/or allyl monomers (diallyl (2,2,4-trimethylhexane-1,6-diyl)dicarbamate), and/or methacrylates (e.g. 1,4-butanediol dimethacrylate, BMA; Isobutylmethacrylat, IsobutylMA; 7,7,9-trimethyl-4,13-dioxo-3,14-dioxa-5,12-diazahexadecane-1,16-diyl bis(2-methylacrylate), UDMA; Neopentyl glycol dimethacrylate, NPGDMA; Trimethylolpropan trimethacrylate, TMPTMA), and/or acrylates (1,4-butanediol diacrylate, BA), and/or vinylethers (1,4-bis(vinyloxy)butane, BuVE). To the formulations 3 wt % Irgacure TPO-L (IrgTPOL), 0.5 wt % pyrogallol, 2 wt % MiramerA99, 0.05 wt % sudan orange were added. The printed samples were post-cured with 405 nm at 100° C. As further reference materials BMA and BA, respectively, and also thiol-ene and thiol-yne formulations (PETMP/Bbut, PETMP/BuVE) with 3 wt % IrgTPOL were used.

Table 2 shows the obtained HDT of the tested specimen.

TABLE 2

| Components (Ratio func. groups) | HDT [° C.] |
|---|---|
| UDMA * | 114 +− 3 |
| PETMP/DBC/NPGDMA/TMPTMA (3:1:2, 1:0, 9) | 171 +− 2 |
| PETMP/DPC/NPGDMA/TMPTMA (3:1:2, 1:0, 9) | 117 +− 2 |
| PETMP/diallyl (2,2,4-trimethylhexane-1,6-diyl)dicarbamate/UDMA (3:2:3)* | 36 +− 2 |
| PETMP/diallyl (2,2,4-trimethylhexane-1,6-diyl)dicarbamate/UDMA (2:2:4)* | 50 +− 1 |
| PETMP/diallyl (2,2,4-trimethylhexane-1,6-diyl)dicarbamate/UDMA (2:1:12)* | 65 +− 2 |
| PETMP/DBC/UDMA (3:1:3) | 50 +− 2 |
| PETMP/DBC/UDMA (2:1:4) | 59 +− 1 |
| PETMP/DBC/UDMA (2:1:12) | 80 +− 3 |
| PETMP/di(but-3-yn-1-yl) (2,2,4-trimethylhexane-1,6-diyl)dicarbamate/UDMA (3:1:3) | 49 +− 2 |
| PETMP/di(but-3-yn-1-yl) (2,2,4-trimethylhexane-1,6-diyl)dicarbamate/UDMA (2:1:4) | 58 +− 1 |
| PETMP/di(but-3-yn-1-yl) (2,2,4-trimethylhexane-1,6-diyl)dicarbamate/UDMA (2:1:12) | 75 +− 3 |

TABLE 2-continued

| Components (Ratio func. groups) | HDT [° C.] |
|---|---|
| BMA* | 53 +− 1 |
| BA* | 82 +− 1 |
| PETMP/Bbut* | 41 +− 2 |
| PETMP/BuVE* | −40 +− 3 |

*Comparative examples

The addition of alkynes and/or alkenes and thiols to (meth)acrylates leads to a decrease of the HDT of the photopolymers, however, the HDT is higher as than comparable thiol-yne and thiol-ene systems. Alkyne monomer-containing mixtures provide a higher HDT than mixtures with alkene monomers.

Example 3

The effect of 0.5 wt % pyrogallol (PY) or/and 2 wt % Miramer A99 (MA99) or/and 0.05 wt % aromatic azo compounds on the stability of formulations containing a methacrylate monomer (glyceryldimethacrylate, GMA), an alkyne monomer (di(prop-2-yn-1-yl) carbonate, DPC) and a thiol monomer (pentaerythritol tetrakis (3-mercaptopropionate), PETMP) was examined by rheological measurements. The formulations were stored for three days at 70° C. The increase in viscosity was monitored every 24 h.

For measuring the viscosity, a MC 200 cone- and plate viscosimeter from Anton Paar GmbH (cone unit MK 22/50 mm, 1°) was used. First, the shear rate was varied with a stepped slope and subsequently the viscosity was determined at a constant shear rate of 300 s$^{-1}$ every 30 seconds. The measurements were carried out at 25° C. The start viscosity of the claimed formulation is 79 mPa*s.

The results of the viscosity measurements are shown in Table 3.

TABLE 3

| | Increase in viscosity [%] | | |
|---|---|---|---|
| Components | 1 day | 2 days | 3 days |
| GMA, DPC, PETMP (3:1:3) | 984 | gelation | — |
| GMA, DPC, PETMP (3:1:3) PY | 217 | 340 | 849 |
| GMA, DPC, PETMP (3:1:3) PY, MA99 | 36 | 77 | 173 |
| GMA, DPC, PETMP (3:1;3) PY, MA99, Sudan 2 | 10 | 12 | 21 |
| GMA, DPC, PETMP (3:1:3) PY, MA99, Sudan orange | 20 | 34 | 52 |
| GMA, DPC, PETMP (3:1:3) PY, MA99, 4-Phenylazophenol | 29 | 59 | 112 |
| GMA, DPC, PETMP (3:1:3) PY, MA99, 2,2-Dihydroxyazobenzene | 8 | 20 | 42 |
| GMA, DPC, PETMP (3:1:3) PY, MA99, Tropaeolin O | 15 | 73 | 126 |
| GMA, DPC, PETMP (3:1:3) PY, MA99, Thiazolylazo Resorcinol | 1 | 6 | 11 |

The measurements show that the increase in viscosity can be significantly reduced by the addition of the tested stabilizers. It should be emphasized that azo compounds with an ortho-hydroxygroup provide the greatest stabilizing effect.

Example 4

The attachment of cells to the surface of various 3D printed structures was determined by means of U-2OS osteosarcoma cells. As a (non-toxic) negative control, a cell culture plate was used. The cells were cultured in 175 cm$^2$ culture flasks (Costar Corning) in McCoy's 5A medium (Thermo Fisher Scientific), 10% fetal bovine serum (Gibco), 2 mM L-glutamine, 1% penicillin/streptomycin at 37±1° C. in air atmosphere+5% CO$_2$ and subcultured at regular intervals. 3*10$^5$ U-2OS cells were seeded in 500 µL per well of a 12-well plate and on the surface of various 3D printed structures of the same size.

After 24 h at 37±1° C. cells were stained with 1 µg/mL Hoechst 33342 for 15 min. Images were taken at an inverted bright field microscope and at a confocal microscope. After that the samples were moved to another well and cells dislodged by trypsin treatment from the surface. The trypsin treatment was stopped by addition of cell culture medium and 50 mL of the cell suspension was counted in the CASY Cell Counter and Analyser System Modell TT (Innovatis).

The total cell number was 450.679 in the controls growing on cell culture plates.

Table 4 shows the determined cell numbers on the sample surfaces.

TABLE 4

| Components (Ratio func. groups) | Cell number |
|---|---|
| PETMP/DBC/BMA (3:1:3) | 374584 |
| PETMP/DBC/BMA/IsobutylMA (3:1:2.7:0.3) | 250149 |
| PETMP/DBC/BMA (2:1:4) | 199858 |
| PETMP/diallyl (2,2,4-trimethylhexane-1,6-diyl)dicarbamate/DBC/BMA (9:2:1:9) | 364289 |
| PETMP/diallyl (2,2,4-trimethylhexane-1,6-diyl)dicarbamate/DBC/BMA/IsobutylMA (9:2:1:8.1:0.9) | 125649 |
| 1,4-butanediol dimethacrylate (reference) | 11568 |
| PETMP/DBC/BA (3:1:3) | 301845 |
| PETMP/DBC/BA/IsobutylMA (3:1:2.7:0.3) | 224519 |
| PETMP/DBC/BA (2:1:4) | 142454 |
| PETMP/diallyl (2,2,4-trimethylhexane-1,6-diyl)dicarbamate/DBC/BA (9:2:1:9) | 284651 |
| PETMP/diallyl (2,2,4-trimethylhexane-1,6-diyl)dicarbamate/DBC/BA/IsobutylMA (9:2:1:8.1:0.9) | 101548 |
| 1,4-butanediol diacrylate (reference) | 7890 |

The growth of U-2OS osteosarcoma cells on the specimens is significantly higher than on the reference material. Particularly good results were achieved with formulations with a high amount of thiol and alkyne or alkene. This can be attributed to the higher conversion of (meth)acrylate monomers and thus to fewer content of free cytotoxic (meth)acrylate monomers in the 3D printed materials.

Example 5

The cytotoxicity of the 3D printed structures was evaluated according to ISO standard 10993-5:2009 using MRC-5 cells. The MRC-5 cells were cultured in 175 cm$^2$ culture flaks (Costar Corning) in Minimal Essential Medium (MEM, Life technologies) and Earl's Salts, 10% fetal bovine serum (Gibco), 2 mM L-glutamine, 1% penicillin/streptomycin at 37±1° C. and 5% CO$_2$. This cell line was derived from normal lung tissue of a 14-week-old male fetus. The printed samples were extracted in cell culture medium for 24 h at 37° C. according to ISO10993-1 guidelines. To obtain subconfluent cultures 8000 MRC-5 cells were seeded per well and cultures 24 h prior to the exposure with the elates of the samples. As a (toxic) positive control, Triton X 100 was added to MRC-5 cells for 10 minutes. As a (non-toxic) negative control, a cell culture medium was used.

After completion of the incubation, the activity of the dehydrogenase as indication for cell viability was calculated. Therefor CellTiter 96 Aqueous Non-Radioactive Cell Proliferation Assay (Promega) was used. The tetrazolium compound in this assay is bioreduced by cellular dehydrogenases into a formazan product that is soluble in tissue culture medium and quantified by absorbance reading. Plates were incubated for 2 h at 37±1° C. and 5% $CO_2$ in a cell incubator. Absorbance was read at 490 nm on a plate reader (SPECTRA MAX plus 384, Molecular Devices).

A reduction of the enzyme content from MRC-5 cells by more than 30%, relative to the negative control, was evaluated as cytotoxic (according to ISO 10993-5:2009).

The results obtained from various mixtures are shown in table 5.

TABLE 5

| Components (Ratio func. groups) | Dehydrogenase activity [%] |
|---|---|
| PETMP/DBC/BMA (3:1:3) | 94.2 |
| PETMP/DBC/BMA/IsobutylMA (3:1:2.7:0.3) | 78.1 |
| PETMP/DBC/BMA (2:1:4) | 71.6 |
| PETMP/diallyl (2,2,4-trimethylhexane-1,6-diyl)dicarbamate/DBC/BMA 9:2:1:9 | 92.1 |
| PETMP/diallyl (2,2,4-trimethylhexane-1,6-diyl)dicarbamate/DBC/BMA/IsobutylMA (9:2:1:8.1:0.9) | 77.9 |
| 1,4-butanediol dimethacrylate (reference) | 40.7 |
| PETMP/DBC/BA (3:1:3) | 85.7 |
| PETMP/DBC/BA/IsobutylMA (3:1:2.7:0.3) | 75.2 |
| PETMP/DBC/BA (2:1:4) | 68.1 |
| PETMP/diallyl (2,2,4-trimethylhexane-1,6-diyl)dicarbamate/DBC/BA (9:2:1:9) | 81.2 |
| PETMP/diallyl (2,2,4-trimethylhexane-1,6-diyl)dicarbamate/DBC/BA/IsobutylMA (9:2:1:8.1:0.9) | 70.4 |
| 1,4-butanediol diacrylate (reference) | 20.3 |

The different formulations show protein activities of over 70% compared to the positive control. Particularly good results were achieved with formulations with a high amount of thiol and alkyne or alkene. This can be attributed to the higher conversion of (meth)acrylate monomers and thus to fewer content of cytotoxic (meth)acrylate monomers in the 3D printed materials.

Example 6a

Selected compositions were modified with an antimicrobial acrylate monomer (N,N-dimethyl-N-(4-methylenehex-5-en-1-yl)hexadecan-1-aminium, DMHA) using the Thiol-Michael reaction under basic conditions. Therefor the 3D printed structures were incubated in a saturated solution of DMHA in ethanol for 24 h at room temperature. To 20 mL of the solution 0.2 mL of trimethylamine were added. After that the samples were washed with ethanol and dried at 50° C. for 6 h.

The antimicrobial effect of the surface modified 3D printed structures was investigated using the two different bacteria strains (Staphylococcus aureus ATCC 6538 and Escherichia coli NCTC 10538). For this purpose, 0.4 mL of germ suspension were pipetted onto the test specimens. One test sample was used immediately after the inoculation for zero-time determination (negative control). The other samples were used after a contact time of 24 h at 37° C. The recovery of the test bacteria from the specimen was carried out by shaking the samples for 2 minutes at 150 rpm in 10 ml of SCDLP medium with glass spheres on a rotary shaker. The determination of the bacterial count of the test specimens was carried out by diluting the eluates. Subsequently the solution was poured over with 1 mL of counting agar.

Table 6 shows the effect of the modification on the bacterial count of Staphylococcus aureus and Escherichia coli.

TABLE 6

| | Decrease in the bacterial count compared to the negative control [%] | |
|---|---|---|
| Components (Ratio func. groups), | Escherichia coli NCTC 10538 | staphylococcus aureus ATCC 6538 |
| PETMP/DBC/BMA (3:1:3) | 99 | 92 |
| PETMP/diallyl (2,2,4-trimethylhexane-1,6-diyl)dicarbamate/BMA (3:2:3) | 98 | 90 |
| PETMP/diallyl (2,2,4-trimethylhexane-1,6-diyl)dicarbamate/DBC/BMA (9:2:1:9) | 99 | 92 |
| PETMP/DBC/BA (3:1:6) | 99 | 95 |
| PETMP/diallyl (2,2,4-trimethylhexane-1,6-diyl)dicarbamate/BA (3:2:3) | 98 | 92 |
| PETMP/diallyl (2,2,4-trimethylhexane-1,6-diyl)dicarbamate/DBC/BA (9:2:1:9) | 99 | 93 |

All modifies samples show significant antibacterial activity against Staphylococcus aureus and Escherichia coli, respectively.

Example 7

The effect of 0.5 wt % pyrogallol (PY) and/or 2 wt % Miramer A99 (MA99) and/or 0.05 wt % aromatic azo compounds on the stability of formulations containing a thiol monomer (pentaerythritol tetrakis (3-mercaptopropionate) and either a monomer containing a terminal C=C double bond or a monomer containing a terminal alkyne group was examined by rheological measurements. The formulations were stored for seven days at 50° C. The increase in viscosity was monitored on day one, three and seven.

For measuring the viscosity, a MC 200 cone- and plate viscosimeter from Anton Paar GmbH (cone unit MK 22/50 mm, 1°) was used. First, the shear rate was varied with a stepped slope and subsequently the viscosity was determined at a constant shear rate of 300 $s^{-1}$ every 30 seconds. The measurements were carried out at 25° C. The results of the viscosity measurements are shown in Table 7.

TABLE 7

| | Increase in viscosity [%] | | |
|---|---|---|---|
| Components (Ratio func. groups) | 1 day | 3 days | 7 days |
| GMA, PETMP (1:1) | 400 | 799 | gelation |
| GMA, PETMP (1:1) PY | 4 | 31 | 51 |
| GMA, PETMP (1:1) Sudan 2 | 5 | 35 | 55 |
| GMA, PETMP (1:1) PY, Sudan 2 | 4 | 15 | 30 |
| GMA, PETMP (1:1) PY, Sudan 2, MA99 | 2 | 5 | 14 |
| DPC, PETMP (1:2) | 164 | 341 | gelation |
| DPC, PETMP (1:2) PY | 5 | 14 | 35 |
| DPC, PETMP (1:2) Sudan 2 | 19 | 26 | 54 |
| DPC, PETMP (1:2) PY, Sudan 2 | 2 | 5 | 12 |
| DPC, PETMP (1:2) PY, Sudan 2, MA99 | 1 | 2 | 5 |

TABLE 7-continued

| Components (Ratio func. groups) | Increase in viscosity [%] | | |
|---|---|---|---|
| | 1 day | 3 days | 7 days |
| BA, PETMP (1:1) | gelation | — | — |
| BA, PETMP (1:1) PY | 214 | 459 | gelation |
| BA, PETMP (1:1) Sudan 2 | 423 | gelation | — |
| BA, PETMP (1:1) PY, Sudan 2 | 124 | 321 | gelation |
| BA, PETMP (1:1) PY, Sudan 2, MA99 | 35 | 126 | 367 |
| diallyl (2,2,4-trimethylhexane-1,6-diyl)dicarbamate, PETMP (1:1) | 523 | gelation | — |
| diallyl (2,2,4-trimethylhexane-1,6-diyl)dicarbamate, PETMP (1:1) PY | 31 | 46 | 61 |
| diallyl (2,2,4-trimethylhexane-1,6-diyl)dicarbamate, PETMP (1:1) Sudan 2 | 35 | 50 | 156 |
| diallyl (2,2,4-trimethylhexane-1,6-diyl)dicarbamate, PETMP (1:1) PY, Sudan 2 | 11 | 29 | 47 |
| diallyl (2,2,4-trimethylhexane-1,6-diyl)dicarbamate, PETMP (1:1) PY, Sudan 2, MA99 | 3 | 8 | 15 |
| 1,4-Butanediol divinyl ether, PETMP (1:1) | gelation | — | — |
| 1,4-Butanediol divinyl ether, PETMP (1:1) PY | 76 | 302 | gelation |
| 1,4-Butanediol divinyl ether, PETMP (1:1) Sudan 2 | 88 | 567 | gelation |
| 1,4-Butanediol divinyl ether, PETMP (1:1) PY, Sudan 2 | 56 | 156 | 586 |
| 1,4-Butanediol divinyl ether, PETMP (1:1) PY, Sudan 2, MA99 | 16 | 54 | 275 |

The measurements show that the increase in viscosity can be significantly reduced by the addition of the tested stabilizers.

Example 8

The effect of 0.5 wt % radical scavenger (pyrogallol [Py] or propylgallate [PYG] or 2,4-dihydroxybenzaldehyde [2,4-DHB] or 3,4-dihydroxybenzaldehyde [3,4-DHB] or 3,5-dihydroxybenzaldehyde [3,5-DHB] or 2,5-dihydroxybenzaldehyde [2,5-DHB] or 2,3-dihydroxybenzaldehyde [2,3-DHB] or 2,3,4-trihydroxybenzaldehyde [2,3,4-THB]) and/or 2 wt % Miramer A99 (MA99) and/or 0.05 wt % complexing agent (sudan II or ammonium oxalate [AO] or ethylenebis(diphenylphosphine) [EBP]) on the stability of formulations containing a thiol monomer (pentaerythritol tetrakis (3-mercaptopropionate) [PETMP]) and a monomer containing a terminal C=C double bond (1,4-butanediol dimethacrylate [BMA] or 1,3,5-Triallyl-1,3,5-triazine-2,4,6 (1H,3H,5H)-trione) and/or a monomer containing a terminal alkyne group (di(prop-2-yn-1-yl) carbonate [DPC]) was examined by rheological measurements. The formulations were stored for 42 days at 50° C. The increase in viscosity was monitored after 42 days.

For measuring the viscosity, a MC 200 cone- and plate viscosimeter from Anton Paar GmbH (cone unit MK 22/50 mm, 1°) was used. First, the shear rate was varied with a stepped slope and subsequently the viscosity was determined at a constant shear rate of 300 s$^1$ every 30 seconds. The measurements were carried out at 25° C. The results of the viscosity measurements are shown in Table 8.

TABLE 8

| Components (Ratio func. groups) | Increase in viscosity [%] after 42 days |
|---|---|
| BMA, DPC, PETMP (3:1:3) | 136 |
| BMA, DPC, PETMP (3:1:3) MA99 | gelation |
| BMA, DPC, PETMP (3:1:3) Sudan 2 | 173 |
| BMA, DPC, PETMP (3:1:3) MA99, Sudan 2 | gelation |
| BMA, DPC, PETMP (3:1:3) PY, MA99, Sudan 2 | −3 |
| BMA, DPC, PETMP (3:1:3) 2,4-DHB, MA99, Sudan 2 | 4 |
| BMA, DPC, PETMP (3:1:3) 3,4-DHB, MA99, Sudan 2 | 9 |
| BMA, DPC, PETMP (3:1:3) 3,5-DHB, MA99, Sudan 2 | 0 |
| BMA, DPC, PETMP (3:1:3) 2,5-DHB, MA99, Sudan 2 | −5 |
| BMA, DPC, PETMP (3:1:3) 2,3-DHB, MA99, Sudan 2 | 10 |
| BMA, DPC, PETMP (3:1:3) 2,3,4-THB, MA99, Sudan 2 | −4 |
| BMA, DPC, PETMP (3:1:3) 2,3,4-THB, MA99 | 2 |
| BMA, 1,3,5-Triallyl-1,3,5-triazine-2,4,6(1H,3H,5H)-trione, PETMP (3:1:2) | gelation |
| BMA, 1,3,5-Triallyl-1,3,5-triazine-2,4,6(1H,3H5H)-trione, PETMP (3:1:2) 2,3,4-THB, MA99 | 4 |
| 1,3,5-Triailyl-1,3,5-triazine-2,4,6(1H,3H,5H)-trione, PETMP (1:1) | gelation |
| 1,3,5-Triailyl-1,3,5-triazine-2,4,6(1H,3H,5H)-trione, PETMP (1:1) PYG, MA99, Sudan 2 | 8 |
| 1,3,5-Triallyl-1,3,5-triazine-2,4,6(1H,3H,5H)-trione, PETMP (1:1) PYG, MA99, AO | 27 |
| 1,3,5-Triallyl-1,3,5-triazine-2,4,6(1H,3H,5H)-trione, PETMP (1:1) PYG, MA99, EPB | 50 |

The measurements show that the increase in viscosity can be significantly reduced by the addition of the tested stabilizers.

Example 9

For the evaluation of the hydrolytic degradation behaviour of the photopolymers, 3D printed specimen were prepared (4×4×1 mm³). The used resins consist of thiol monomers (e.g. pentaerythritol tetrakis(3-mercaptopropionate), PETMP), alkyne monomers (e.g. 1,4-butanediol dibut-1-ynyl ether, BBut) and methacrylates (e.g. 1,4-butanediol dimethacrylate, BMA). To the formulations 3 wt % Irgacure TPO-L (IrgTPOL), 0.5 wt % pyrogallol, 2 wt % MiramerA99, 0.05 wt % sudan orange were added. The printed samples were post-cured with 405 nm at 100° C. As reference materials BMA and BA, respectively, with 3 wt % IrgTPOL were used.

The ratios of the functional groups of the monomers are listed in brackets in table 9.

The samples were immersed in 1 M NaOH, at 45° C. under continuous shaking. The sample dry weight was monitored over the test period.

Table 9 shows the weight loss after 3, 5 and 7 days.

TABLE 9

| Components (Ratio func. groups) | Weight loss [%] | | |
| --- | --- | --- | --- |
| | 3 day | 5 days | 7 days |
| PETMP/Bbut/BMA (3:1:3) | 31.5 | 77.9 | 99.8 |
| PETMP/Bbut/BMA (2:1:4) | 7.4 | 24.4 | 64.7 |
| PETMP/Bbut/BMA (2:1:12) | 5.4 | 12.2 | 42.8 |
| BMA* | 0.8 | 1.6 | 3.9 |

* Comparative examples

Example 10

Photorheology measurements were conducted on an Anton Paar MCR 302 WESP rheometer coupled with a Bruker Vertex 80 FTIR spectrometer using an NIR light source and $CaF_2$ beam splitter. The IR beam is guided through the sample, which is being analyzed by rheology, with external mirrors. The rheometer is equipped with a P-PTD 200/GL Peltier glass plate and a PP25 measuring system, which reflects the IR beam into an external MCT-detector. For protection of the measurement set-up a PE tape was placed in between sample and glass plate due to the good adhesion of the thiol/yne/ene materials to the glass surface.

The resins according to embodiments of the invention comprise the thiol monomer pentaerythritol tetrakis(3-mercaptopropionate), (PETMP), the alkene monomer urethane dimethacrylate (UDMA) and the alkyne monomer di(but-3-yn-1-yl) carbonate (DBC), whereas the resins according to comparative examples comprise the thiol monomer PETMP and either the alkene monomer UDMA or the alkyne monomer DBC.

To the formulations 3 wt % Irgacure TPO-L (IrgTPOL) and 0.2 wt % lauryl gallate were added. For all measurements approximately 150 µl of resin formulation were used and the measurements were performed at 20° C. with a measurement gap of 200 µm. Rheological measurements were conducted in oscillation mode with a strain of 1% and a frequency of 1 Hz. The materials were cured from the underside of the glass plate using an Exfo Omnicure S 2000 with a broadband Hg-lamp and a double waveguide to ensure homogeneous irradiation (300 s, 320-500 nm, 15 W $cm^2$ on the surface of the sample). During photopolymerization the storage and loss moduli were recorded with a frequency of 5 Hz during the first minute and then 1 Hz for the last 4 min of UV irradiation. IR measurements were recorded every ~0.26 s and the measurements were started 5 s prior to UV irradiation. The conversion of the methacrylate was evaluated by following the decrease of the respective NIR signals (6164 $cm^1$ for methacrylate).

The thermomechanical properties of the 3D printed resins were measured in tension mode using a DMA/SDTA 861 (Mettler Toledo) with a heating rate of 2 K $min^{-1}$ in the temperature range from −40 to 120° C. The operating frequency was determined at 1 Hz. For comparison of the polymer samples, the storage modulus was evaluated at room temperature (20° C.).

Table 10 shows the results from RT-NIR-photorheology and DMA measurements.

TABLE 10

| | Components (Ratio func. groups) | $t_g$/ s | CMA/ % | $F_N$/ N | Modulus/ MPa |
| --- | --- | --- | --- | --- | --- |
| M1* | PETMP/DBC (2:1) | 8.1 | | 15.1 | 1475.6 |
| M2 | PETMP/UDMA/DBC (8:2:3) | 9.0 | 99.8 | 13.8 | 178.6 |
| M3 | PETMP/UDMA/DBC (4:2:1) | 6.6 | 99.8 | 14.0 | 72.8 |
| M4 | PETMP/UDMA/DBC (8:6:1) | 3.9 | 98.1 | 14.4 | 33.0 |
| M5* | PETMP/UDMA (4:4) | 3.4 | 98.7 | 13.8 | 17.6 |
| M6 | PETMP/UDMA/DBC (6:4:3) | 5.7 | 96.9 | 14.0 | 1531.4 |
| M7 | PETMP/UDMA/DBC (3:3:1) | 3.7 | 95.0 | 14.8 | 2014.9 |
| M8 | PETMP/UDMA/DBC (6:8:1) | 3.0 | 95.2 | 15.6 | 1649.1 |
| M9* | PETMP/UDMA (3:5) | 2.6 | 96.1 | 16.1 | 1015.6 |
| M10 | PETMP/UDMA/DBC (2:4:1) | 3.0 | 87.9 | 16.5 | 2686.7 |
| M11 | PETMP/UDMA/DBC (4:10:1) | 2.6 | 86.1 | 17.1 | 2755.1 |
| M12* | PETMP/UDMA 1:3) | 2.0 | 79.3 | 16.8 | 2741.1 |
| M13 | PETMP/UDMA/DBC (2:12:1) | 2.0 | 80.9 | 17.0 | 3063.4 |
| M14 | PETMP/UDMA/DBC (1:7:0) | 2.2 | 77.1 | 15.8 | 2978.6 |
| M15* | PETMP/UDMA (0:1) | 2.0 | 70.4 | 18.1 | 3060.9 | tg . . . time of gelation (gel point)
CMA . . . final methacrylate conversion
FN . . . normal force
*Comparative examples The time of gelation can be tuned by the addition of thiol and alykne to the methacrylate. The tested resin compositions according to embodiments of the invention (thiol/alkyne/methacrylate, e.g. M10) provides a significantly higher methacrylate conversion (87.9% vs. 70.4%) than the polymerization of pure methacrylate (M15). The addition of the alkyne and the thiol (e.g. M10) leads to less shrinkage stress (is proportional to the normal force FN) compared to the polymerization of pure methacrylate (M15; 16.5 N vs. 18.1 N). Cured formulations with thiol, alkyne and methacrylate (e.g. M7) leads to a higher modulus compared to corresponding samples without alkyne (e.g. M5 and M9 respectively).

Example 11

For the evaluation of the cleaning efficiency and thus the removal of residual non-cured UV resin from the printed structures the following test was performed.

The printed specimen were prepared (20×10×2 $mm^3$). The used resins contain pentaerythritol tetrakis(3-mercaptopropionate) (PETMP), 1,4-butanediol dibut-1-ynyl ether (BBut) and 1,4-butanediol dimethacrylate (BMA). To the formulations 3 wt % Irgacure TPO-L (IrgTPOL), 0.5 wt % pyrogallol, 2 wt % MiramerA99 and 0.05 wt % sudan II were added.

After the printing step the printed structures were immersed into the cleaning solution using glass vials. The cleaning solution contained 40 wt % of Concentryl® (available from Becker Chemie GmbH), 30 wt % of water and 30 wt. % of 2-propanol.

In a subsequent step the vials were transferred in an ultrasonic bath (Bandelin sonorex digitec) for 5 minutes and a water temperature of 50° C. Afterwards the cleaning procedure was evaluated by inspection of both printed part and cleaning solution.

After 5 minutes of immersion, no residuals remained on the printed structure and and the cleaning solution became a clear bright liquid with solid polymer particles at the bottom of the vial.

In the following, various exemplary embodiments of the invention are summarized:

Embodiment 1. A resin composition comprising:
- at least one compound C1 having at least one terminal alkyne functional group;
- at least one compound C2 having at least two thiol functional groups;
- at least one compound C3 having at least one carbon-carbon double bond;
- at least one photoinitiator; and
- at least one stabilizer.

Embodiment 2. The resin composition according to embodiment 1, wherein the at least one compound C1 has at least one terminal alkyne functional group and at least one selected from a linear or branched, saturated or unsaturated, substituted or unsubstituted alkyl group; a linear or branched, saturated or unsaturated, substituted or unsubstituted heteroalkyl group; a saturated or unsaturated, substituted or unsubstituted cycloalkyl group; a saturated or unsaturated, substituted or unsubstituted heterocycloalkyl group; a substituted or unsubstituted aryl group; a substituted or unsubstituted heteroaryl group; a linear or branched, substituted or unsubstituted aralkyl group; a linear or branched, substituted or unsubstituted alkaryl group; an oligomer or a polymer.

Embodiment 3. The resin composition according to embodiment 1 or 2, wherein the at least one compound C1 has at least one terminal alkyne functional group selected from the group consisting of propargyl, butynyl and pentynyl.

Embodiment 4. The resin composition according to any one of the preceding embodiments, wherein the at least one compound C1 has at least one terminal alkyne functional group and at least one functional group selected from the group consisting of a carbonate, a carbamate, an ether and an ester.

Embodiment 5. The resin composition according to any one of the preceding embodiments, wherein the at least one compound C1 comprises a compound having a functional group selected from the group consisting of a propargyl carbonate, a propargyl carbamate, a propargyl ether, a propargyl ester, a butynyl carbonate, a butynyl carbamate, a butynyl ether, a butynyl ester, a pentynyl carbonate, a pentynyl carbamate, a pentynyl ether, and a pentynyl ester.

Embodiment 6. The resin composition according to any one of the preceding embodiments, wherein the at least one compound C1 has one terminal alkyne functional group.

Embodiment 7. The resin composition according to any one of the embodiments 1 to 5, wherein the at least one compound C1 has at least two terminal alkyne functional groups.

Embodiment 8. The resin composition according to any one of the preceding embodiments, wherein at least one of the thiol functional groups comprises a thiol protecting group.

Embodiment 9. The resin composition according to embodiment 8, wherein the thiol protection group is selected from the group consisting of an acyl group, a silyl group and a siloxyl group.

Embodiment 10. The resin composition according to embodiment 8 or 9, wherein the resin composition further comprises at least one photoacid and/or at least one photobase.

Embodiment 11. The resin composition according to any one of the preceding embodiments, wherein the at least one compound C2 is represented by the following general formula (XIII):

wherein
- z represents an integer of from 2 to 1000;
- Z represents—independently from each other on each occurrence—hydrogen or a thiol protecting group;
- L represents—independently from each other on each occurrence—a single bond or a divalent group selected from the group consisting of a linear or branched, saturated or unsaturated, substituted or unsubstituted alkylene group; a linear or branched, saturated or unsaturated, substituted or unsubstituted heteroalkylene group; a saturated or unsaturated, substituted or unsubstituted cycloalkylene group; a saturated or unsaturated, substituted or unsubstituted heterocycloalkylene group; a substituted or unsubstituted arylene group; a substituted or unsubstituted heteroarylene group; a linear or branched, substituted or unsubstituted aralkylene group; a linear or branched, substituted or unsubstituted alkarylene group; or a silicium containing divalent group; and
- X represents a z-valent group selected from the group consisting of a linear or branched, saturated or unsaturated, substituted or unsubstituted alkyl group; a linear or branched, saturated or unsaturated, substituted or unsubstituted heteroalkyl group; a saturated or unsaturated, substituted or unsubstituted cycloalkyl group; a saturated or unsaturated, substituted or unsubstituted heterocycloalkyl group; a substituted or unsubstituted aryl group; a substituted or unsubstituted heteroaryl group; a linear or branched, substituted or unsubstituted aralkyl group; a linear or branched, substituted or unsubstituted alkaryl group; or a silicium containing z-valent group.

Embodiment 12. The resin composition according to any one of the preceding embodiments, wherein the at least one compound C3 having at least one carbon-carbon double bond has at least one functional group selected from the group consisting of a vinyl functional group, an allyl functional group, an acrylate functional group and a methacrylate functional group.

Embodiment 13. The resin composition according to embodiment 12, wherein the least one compound C3 having at least one carbon-carbon double bond has at least one vinyl functional group and/or allyl functional group.

Embodiment 14. The resin composition according to embodiment 12 or 13, wherein the least one compound C3 having at least one carbon-carbon double bond has at least one (meth)acrylate functional group.

Embodiment 15. The resin composition according to any one of the preceding embodiments, wherein the at least one compound C3 has at least two carbon-carbon double bonds, in particular at least two functional groups selected from the group consisting of a vinyl functional group, an allyl functional group, an acrylate functional group and a methacrylate functional group.

Embodiment 16. The resin composition according to any one of the preceding embodiments, wherein the composition comprises from 5 to 80 wt.-% of the at least one compound C1.

Embodiment 17. The resin composition according to any one of the preceding embodiments, wherein the composition comprises from 5 to 80 wt.-% of the at least one compound C2.

Embodiment 18. The resin composition according to any one of the preceding embodiments, wherein the composition comprises from 10 to 90 wt.-% of the at least one compound C3.

Embodiment 19. The resin composition according to any one of the preceding embodiments, wherein the photoinitiator is an ultraviolet-active photoinitiator and/or a visible light-active photoinitiator.

Embodiment 20. The resin composition according to any one of the preceding embodiments, wherein the composition comprises from 0.1 to 20 wt.-% of the at least one photoinitiator.

Embodiment 21. The resin composition according to any one of the preceding embodiments, wherein the at least one stabilizer comprises at least one radical scavenger, in particular at least one phenolic radical scavenger.

Embodiment 22. The resin composition according to any one of the preceding embodiments, wherein the at least one stabilizer comprises at least one phosphorous containing compound, in particular at least one phosphonic acid and/or at least one phosphoric acid and/or a derivative thereof.

Embodiment 23. The resin composition according to any one of the preceding embodiments, wherein the at least one stabilizer comprises at least one complexing agent, in particular at least one aromatic azo compound, more specifically at least one aromatic azo compound having a hydroxy group in ortho-position with regard to an azo group.

Embodiment 24. The resin composition according to any one of the preceding embodiments, wherein the at least one stabilizer comprises:
at least one radical scavenger, in particular at least one phenolic radical scavenger, and
at least one phosphorous containing compound, in particular at least one phosphonic acid and/or at least one phosphoric acid and/or a derivative thereof.

Embodiment 25. The resin composition according to any one of the embodiments 1 to 23, wherein the at least one stabilizer comprises:
at least one radical scavenger, in particular at least one phenolic radical scavenger, and
at least one complexing agent, in particular at least one aromatic azo compound.

Embodiment 26. The resin composition according to any one of the preceding embodiments, wherein the at least one stabilizer comprises:
at least one radical scavenger, in particular at least one phenolic radical scavenger,
at least one phosphorous containing compound, in particular at least one phosphonic acid and/or at least one phosphoric acid and/or a derivative thereof, and
at least one complexing agent, in particular at least one aromatic azo compound.

Embodiment 27. The resin composition according to any one of the preceding embodiments, wherein the composition comprises from 0.001 to 10 wt.-% of the at least one stabilizer.

Embodiment 28. The resin composition according to any one of the preceding embodiments, wherein the composition further comprises at least one additive selected from the group consisting of a pigment, an inorganic filler, an organic filler, a dispersing agent, a levelling agent, a slip agent, a light absorber, a rheology modifier and a defoaming additive.

Embodiment 29. The resin composition according to embodiment 28, wherein the composition comprises from 0.1 to 70 wt.-% of the at least one additive.

Embodiment 30. The resin composition according to any one of the preceding embodiments, wherein the composition is substantially solvent-free, in particular substantially water-free.

Embodiment 31. The resin composition according to any one of the preceding embodiments, wherein the at least one compound C3 having at least one carbon-carbon double bond has at least one functional group selected from the group consisting of an allyl functional group, an acrylate functional group and a methacrylate functional group, and
wherein the composition is substantially solvent-free, in particular substantially water-free.

Embodiment 32. The resin composition according to any one of the preceding embodiments, wherein the at least one compound C1 and the at least one compound C3 form one compound C4 having at least one terminal alkyne functional group and at least one carbon-carbon double bond.

Embodiment 33. Use of a resin composition as defined in any one embodiments 1 to 32 as or in an ink.

Embodiment 34. A kit, in particular a kit-of-parts, comprising
at least one compound C1 having at least one terminal alkyne functional group;
at least one compound C2 having at least two thiol functional groups;
at least one compound C3 having at least one carbon-carbon double bond;
at least one photoinitiator; and
optionally at least one stabilizer.

Embodiment 35. Use of a kit as defined in embodiment 34 for preparing a resin composition for use as or in an ink.

Embodiment 36. A printing method comprising the steps of
providing a first ink portion comprising at least one compound C1 having at least one terminal alkyne functional group and at least one compound C3 having at least one carbon-carbon double bond;
providing a second ink portion comprising at least one compound C2 having at least two thiol functional groups;
wherein at least one of the first and the second ink portion further comprises at least one photoinitiator;
forming a resin composition from the first and the second ink portion, immediately followed by irradiating at least a part of the resin composition with an energy-carrying activation beam so as to cause polymerization of the at least a part of the resin composition and so as to obtain a polymer.

Embodiment 37. The printing method according to embodiment 36, wherein at least one of the first and the second ink portion further comprises at least one stabilizer.

Embodiment 38. The printing method according to embodiment 36 or 37, wherein the method further comprises the step of
heating the first ink portion and/or the second ink portion, in particular before and/or upon providing the first ink portion and/or the second ink portion.

Embodiment 39. A printing method comprising the steps of
providing a resin composition as defined in any one embodiments 1 to 32; and
irradiating at least a part of the resin composition with an energy-carrying activation beam so as to cause polymerization of the at least a part of the resin composition and so as to obtain a polymer.

Embodiment 40. The printing method according to embodiment 39, wherein the method further comprises the step of
heating the resin composition, in particular before and/or upon providing the resin composition.

Embodiment 41. The printing method according to any one of embodiments 36 to 40, wherein the printing method is a three-dimensional printing method.

Embodiment 42. The printing method according to embodiment 41, wherein the three-dimensional printing method is any one selected from the group consisting of stereolithography (SLA), two-photon absorption (TPA) polymerization, digital light processing (DLP), reactive laser sintering (RLS), solid ground curing (SGC), multi jet modeling (MJM) or a combination thereof.

Embodiment 43. The printing method according to any one of embodiments 36 to 42, further comprising a step of post-curing the polymer during and/or after irradiating the at least part of the resin composition.

Embodiment 44. The printing method according to any one of embodiments 36 to 43, wherein the energy-carrying activation beam comprises electromagnetic radiation, in particular selected from the group consisting of ultraviolet radiation and visible light radiation.

Embodiment 45. The printing method according to any one of embodiments 36 to 44, wherein the printing method is a solvent-free printing method.

Embodiment 46. The printing method according to any one of embodiments 36 to 45, further comprising a step of cleaning the polymer.

Embodiment 47. The printing method according to embodiment 46, wherein the step of cleaning comprises contacting the polymer with a cleaning composition comprising an alkaline compound, a surfactant and an appropriate solvent.

Embodiment 48. A polymer obtainable by the printing method according to any one of embodiments 36 to 47.

Embodiment 49. An article comprising or formed from the polymer according to embodiment 48.

Embodiment 50. The article according to embodiment 49, wherein the article is a medical device or a biomedical device, in particular selected from the group consisting of an implant, a bone substitute, a tissue substitute and a dental product.

Embodiment 51. The article according to embodiment 49 or 50, wherein a surface of the article is modified by a coating, in particular an antimicrobial coating.

Embodiment 52. The article according to any one of embodiments 49 to 51, wherein the article is a shape memory article.

Embodiment 53. Use of a polymer according to embodiment 48 or of an article according to any one of embodiments 49 to 52 in a medical or biomedical application.

Embodiment 54. The use according to embodiment 53, wherein the medical or biomedical application comprises any one selected from the group consisting of an implantation, a bone substitution or replacement, a tissue substitution or replacement, and a dental application.

Embodiment 55. A composition comprising:
at least one compound C1 having at least one terminal alkyne functional group and/or at least one compound C3 having at least one carbon-carbon double bond;
at least one compound C2 having at least two thiol functional groups; and
at least one stabilizer selected from the group consisting of a radical scavenger, a phosphorous containing compound and a complexing agent.

Embodiment 56. The composition according to embodiment 55, wherein the at least one stabilizer comprises at least one radical scavenger, in particular at least one phenolic radical scavenger.

Embodiment 57. The composition according to embodiment 55 or 56, wherein the at least one stabilizer comprises at least one phosphorous containing compound, in particular at least one phosphonic acid and/or at least one phosphoric acid and/or a derivative thereof.

Embodiment 58. The composition according to any one of embodiments 55 to 57, wherein the at least one stabilizer comprises at least one complexing agent, in particular at least one aromatic azo compound, more specifically at least one aromatic azo compound having a hydroxy group in ortho-position with regard to an azo group.

Embodiment 59. The composition according to any one of embodiments 55 to 58, wherein the at least one stabilizer comprises:
at least one radical scavenger, in particular at least one phenolic radical scavenger, and
at least one phosphorous containing compound, in particular at least one phosphonic acid and/or at least one phosphoric acid and/or a derivative thereof.

Embodiment 60. The composition according to any one of embodiments 55 to 58, wherein the at least one stabilizer comprises:
at least one radical scavenger, in particular at least one phenolic radical scavenger, and
at least one complexing agent, in particular at least one aromatic azo compound.

Embodiment 61. The composition according to any one of embodiments 55 to 60, wherein the at least one stabilizer comprises:
at least one radical scavenger, in particular at least one phenolic radical scavenger,
at least one phosphorous containing compound, in particular at least one phosphonic acid and/or at least one phosphoric acid and/or a derivative thereof, and
at least one complexing agent, in particular at least one aromatic azo compound.

Embodiment 62. A printing method comprising the steps of
providing a resin composition comprising
(i) at least one compound C1 having at least one terminal alkyne functional group and/or at least one compound C3 having at least one carbon-carbon double bond and
(ii) at least one compound C2 having at least two thiol functional groups;
irradiating at least a part of the resin composition with an energy-carrying activation beam so as to cause polymerization of the at least a part of the resin composition and so as to obtain a polymer; and
contacting the polymer with a cleaning composition comprising an alkaline compound, a surfactant and a solvent.

Embodiment 63. The printing method according to embodiment 62, wherein the step of contacting the polymer with a cleaning composition is carried out at a temperature of from 20° C. to 60° C. and/or upon application of ultrasonics.

Embodiment 64. The printing method according to embodiment 62 or 63, wherein the alkaline compound comprises an inorganic alkaline compound and/or an organic alkaline compound.

Embodiment 65. The printing method according to any one of embodiments 62 to 64, wherein the alkaline compound is selected from the group consisting of alkali metal carbonates, alkali metal hydroxides, ammonium hydroxide, ammonia, ammonium derivatives, organic amines, such as ethanolamine, and combinations thereof.

Embodiment 66. The printing method according to any one of embodiments 62 to 65, wherein the surfactant is selected from the group consisting of anionic surfactants, zwitterionic surfactants, amphoteric surfactants, nonionic surfactants, cationic surfactants, such as monovalent cationic surfactants, and combinations thereof.

Embodiment 67. The printing method according to any one of embodiments 62 to 66, wherein the solvent comprises a polar solvent and/or an apolar solvent.

Embodiment 68. The printing method according to any one of embodiments 62 to 67, wherein the solvent is selected from the group consisting of water, an alcohol, an ether, an ester, a carbonate, a halogenated alkane, a nitrile, an aldehyde, a ketone, an amide solvent, a sulfoxide, an acid, a hydrocarbon, an aromatic solvent, and combinations thereof.

Embodiment 69. The printing method according to embodiments 62 to 68, wherein the method further comprises, after the step of contacting the polymer with a cleaning composition, a step of removing solids from the cleaning composition.

Embodiment 70. The printing method according to embodiment 69, wherein the step of removing solids from the cleaning composition comprises at least one of filtration, centrifugation and/or decantation of the cleaning composition.

While embodiments of the invention have been described in detail by way of specific embodiments and examples, the invention is not limited thereto and various alterations and modifications are possible, without departing from the scope of the invention.

The invention claimed is:

1. A composition comprising:
    at least one compound C1 having at least one terminal alkyne functional group and/or at least one compound C3 having at least one carbon-carbon double bond;
    at least one compound C2 having at least two thiol functional groups;
    at least one stabilizer selected from the group consisting of a radical scavenger, a phosphorous containing compound and a complexing agent; and
    a light absorber,
    wherein the at least one stabilizer comprises at least one phosphorous containing compound, and wherein the at least one phosphorous containing compound comprises at least one phosphoric acid ester.

2. The composition according to claim 1, wherein the composition comprises at least one compound C1 having at least one terminal alkyne functional group and at least one compound C3 having at least one carbon-carbon double bond.

3. The composition according to claim 1, wherein the at least one compound C1 comprises at least one of the following features:

at least one terminal alkyne functional group and at least one selected from a linear or branched, saturated or unsaturated, substituted or unsubstituted alkyl group; a linear or branched, saturated or unsaturated, substituted or unsubstituted heteroalkyl group; a saturated or unsaturated, substituted or unsubstituted cycloalkyl group; a saturated or unsaturated, substituted or unsubstituted heterocycloalkyl group; a substituted or unsubstituted aryl group; a substituted or unsubstituted heteroaryl group; a linear or branched, substituted or unsubstituted aralkyl group; a linear or branched, substituted or unsubstituted alkaryl group; an oligomer or a polymer; and/or at least one terminal alkyne functional group selected from the group consisting of propargyl, butynyl and pentynyl; and/or at least one terminal alkyne functional group and at least one functional group selected from the group consisting of a carbonate, a carbamate, an ether and an ester; and/or a compound having a functional group selected from the group consisting of a propargyl carbonate, a propargyl carbamate, a propargyl ether, a propargyl ester, a butynyl carbonate, a butynyl carbamate, a butynyl ether, a butynyl ester, a pentynyl carbonate, a pentynyl carbamate, a pentynyl ether, and a pentynyl ester; and/or one terminal alkyne functional group or at least two terminal alkyne functional groups.

4. The resin composition according to claim 1, wherein the at least one compound C2 is represented by the following general formula (XIII):

wherein z represents an integer of from 2 to 1000;

Z represents—independently from each other on each occurrence—hydrogen or a thiol protecting group;

L represents—independently from each other on each occurrence—a single bond or a divalent group selected from the group consisting of a linear or branched, saturated or unsaturated, substituted or unsubstituted alkylene group; a linear or branched, saturated or unsaturated, substituted or unsubstituted heteroalkylene group; a saturated or unsaturated, substituted or unsubstituted cycloalkylene group; a saturated or unsaturated, substituted or unsubstituted heterocycloalkylene group; a substituted or unsubstituted arylene group; a substituted or unsubstituted heteroarylene group; a linear or branched, substituted or unsubstituted aralkylene group; a linear or branched, substituted or unsubstituted alkarylene group; or a silicium containing divalent group; and X represents a z-valent group selected from the group consisting of a linear or branched, saturated or unsaturated, substituted or unsubstituted alkyl group; a linear or branched, saturated or unsaturated, substituted or unsubstituted heteroalkyl group; a saturated or unsaturated, substituted or unsubstituted cycloalkyl group; a saturated or unsaturated, substituted or unsubstituted heterocycloalkyl group; a substituted or unsubstituted aryl group; a substituted or unsubstituted heteroaryl group; a linear or branched, substituted or unsubstituted aralkyl group; a linear or branched, substituted or unsubstituted alkaryl group; or a silicium containing z-valent group.

5. The composition according to claim 1, wherein the at least one compound C3 comprises at least one of the following features:
 at least one functional group selected from the group consisting of a vinyl functional group, an allyl functional group, an acrylate functional group and a methacrylate functional group; and/or
 at least two carbon-carbon double bonds.

6. The composition according to claim 1, wherein the composition comprises at least two compounds C3 including a compound C3a having at least one methacrylate functional group and a compound C3b having at least one allyl functional group.

7. The composition according to claim 1, wherein the at least one stabilizer further comprises at least one radical scavenger.

8. The composition according to claim 1, wherein the at least one stabilizer further comprises at least one complexing agent.

9. The composition according to claim 1, wherein the at least one stabilizer comprises at least one aromatic azo compound having a hydroxy group in ortho-position with regard to an azo group.

10. The composition according to claim 1, wherein the at least one stabilizer further comprises:
 at least one radical scavenger, and
 at least one complexing agent.

11. The composition according to claim 1, further comprising at least one photoinitiator.

12. The composition according to claim 1, wherein the composition comprises at least one of the following features:
 the composition comprises from 0.001 to 10 wt. % of the at least one stabilizer; and/or
 the composition further comprises at least one additive selected from the group consisting of a pigment, an inorganic filler, an organic filler, a dispersing agent, a levelling agent, a slip agent, a rheology modifier and a defoaming additive; and/or
 the composition is substantially solvent-free.

13. A kit comprising:
 at least one compound C1 having at least one terminal alkyne functional group and/or at least one compound C3 having at least one carbon-carbon double bond;
 at least one compound C2 having at least two thiol functional groups;
 at least one stabilizer selected from the group consisting of a radical scavenger, a phosphorous containing compound and a complexing agent; and
 a light absorber,
 wherein the at least one stabilizer comprises at least one phosphorous containing compound, and wherein the at least one phosphorous containing compound comprises at least one phosphoric acid ester.

14. A printing method comprising the steps of:
 providing a resin composition as defined in claim 1, the resin composition further comprising at least one photoinitiator; and
 irradiating at least a part of the resin composition with an energy-carrying activation beam so as to cause polymerization of the at least a part of the resin composition and so as to obtain a polymer.

15. The printing method according to 14, wherein the method further comprises at least one of the following steps:
 heating the resin composition; and/or
 post-curing the polymer during and/or after irradiating the at least part of the resin composition; and/or
 cleaning the polymer.

16. The printing method according to 14, further comprising a step of cleaning the polymer, wherein the step of cleaning comprises contacting the polymer with a cleaning composition comprising an alkaline compound, a surfactant and an appropriate solvent.

17. The printing method according to 14, wherein the method comprises at least one of the following features:
 the printing method is a three-dimensional printing method; and/or
 the printing method is a solvent-free printing method; and/or
 the energy-carrying activation beam comprises electromagnetic radiation.

18. A polymer obtainable by the printing method according to claim 14.

* * * * *